(12) United States Patent
McArthur et al.

(10) Patent No.: US 7,645,587 B2
(45) Date of Patent: Jan. 12, 2010

(54) CANCER-ASSOCIATED ANTIGENS AND METHODS OF THEIR IDENTIFICATION AND USE

(75) Inventors: James McArthur, San Carlos, CA (US); Ju-Fay Chang, San Jose, CA (US); Dale Ando, Walnut Creek, CA (US); Margo Roberts, Charlottesville, VA (US); Jonathan Simons, Baltimore, MD (US); William Nelson, Towson, MD (US)

(73) Assignees: BioSante Pharmaceuticals, Inc., Lincolnshire, IL (US); John Hopkins University, Baltimore, MD (US)

( * ) Notice: Subject to any disclaimer, the term of this patent is extended or adjusted under 35 U.S.C. 154(b) by 0 days.

(21) Appl. No.: 11/799,584

(22) Filed: May 2, 2007

(65) Prior Publication Data
US 2007/0212739 A1    Sep. 13, 2007

Related U.S. Application Data

(63) Continuation of application No. 11/274,856, filed on Nov. 16, 2005, now Pat. No. 7,226,606, which is a continuation of application No. 09/610,891, filed on Jul. 6, 2000, now Pat. No. 7,217,421, which is a continuation of application No. 09/433,391, filed on Nov. 3, 1999, now abandoned.

(60) Provisional application No. 60/106,795, filed on Nov. 3, 1998.

(51) Int. Cl.
*G01N 33/53* (2006.01)

(52) U.S. Cl. ....................................... 435/7.1
(58) Field of Classification Search ........................ None
See application file for complete search history.

(56) References Cited

U.S. PATENT DOCUMENTS

| | | | |
|---|---|---|---|
| 4,931,275 A | 6/1990 | Shinitzky et al. |
| 5,078,996 A | 1/1992 | Conlon, III et al. |
| 5,098,702 A | 3/1992 | Zimmerman et al. |
| 5,637,483 A | 6/1997 | Dranoff et al. |
| 5,674,486 A | 10/1997 | Sobol et al. |
| 5,763,155 A | 6/1998 | Boon-Falleur et al. |
| 5,904,920 A | 5/1999 | Dranoff et al. |
| 2004/0121300 A1 | 6/2004 | Frey et al. |

FOREIGN PATENT DOCUMENTS

WO   WO 98/04282   2/1998

OTHER PUBLICATIONS

Weiner et al., Expert Rev. Vaccines, Oct. 2002;1(3):257-60.*
Alexander et al., "TIL from renal-cell carcinoma: restimulation with tumor influences proliferation and cytolytic activity," *Int. J. Cancer,* 45:119-124 (1990).
Amico et al., "Comparison of phospatase isoenzymes PAP and PSA with bone scan in patients with prostate carcinoma," *Clinical Nuclear Medicine,* 16:643-648 (1991).
Asher et al., "Murine tumor cells transduced with the gene for tumor necrosis factor-alpha. Evidence for paracrine immune effects of tumor necrosis factor against tumors," *J. Immunology,* 146:3227-3234 (1991).
Belldegrun et al., "Interleukin 2 expanded tumor-infiltrating lymphocytes in human renal cell cancer: Isolation, characterization, and antitumor activity," *Cancer Res.,* 48:206-214 (1988).
Belldegrun et al., "Lymphokine mRNA profile and functional analysis of a human CD4+ clone with unique antitumor specificity isolated from renal cell carcinoma ascitic fluid," *Cancer Immunol. Immunother.* 31:1-10 (1990).
Benet et al., "Pharmocokinetics: the dynamics of drug absorption, distribution and elimination," In Goodman & Gilman's: *The Pharmacological Basis of Therapeutics,* Gilman, Rail, Nies, Taylor (eds.), Pergamon Press, 8th ed., 3-32 (1990).
Borrello et al., "A universal granulocyte-macrophage colony-stimulating factor-producing bystander cell line for ues in the formulation of autologous tumor cell-based vaccines," *Human Gene Therapy,* 10:1983-1991 (1999).
Crowley et al., "Human xenograft-nude mouse model of adoptive immunotherapy with human melanoma-specific cytotoxic cells," *Cancer Res.* 52:394-399 (1992).
Darrow et al., "The role of HLA class I antigens in recognition of melanoma cells by tumor-specific cytotoxic T lymphocytes," *J. Immun.,* 142:3329-3335 (1989).
Devita et al., "Chapter 4: Biology of cytokines: the interleukins," "Chapter 5: Principles of tumor immunity: immunocompetence and cancer," "Chapter 6: Principles of Tumor Immunity: Immunocompetence and Cancer," in *Biological Therapy of Cancer,* J.B. Lippincott, Philadelphia, 87-118 (1991).
Dranoff et al., "Vaccination with irradiated tumor cells engineered to secrete murine granulocyte-macropahge colony-stimulating factor stimulates potent, specific, and long-lasting and tumor immunity," *Proc. Natl. Acad. Sci. USA.,* 90:3539-3543 (1993).
Dummer, "GVAX (Cell Genesys)," *Curr Opin Investig Drugs.,* 2:844-848 (2001).
Ezzell, "Cancer 'vaccines;' An idea whose time has come?," *J. NIH Res.,* 7:46-49 (1995).
Fearon et al., "Interleukin-2 production by tumor cells bypasses T helper function in the generation of an antitumor response," Cell, 60:397-403 (1990).
Forni et al., "Helper strategy in tumor immunology: expansion of helper lymphocytes and utilization of helper lymphokines for experimental and clinical immunotherapy," *Cancer and Metastasis Review,* 7:289-309 (1988).

(Continued)

*Primary Examiner*—Misook Yu
(74) *Attorney, Agent, or Firm*—Ropes & Gray LLP; James F. Haley, Jr.; Connie Wong

(57) ABSTRACT

The present invention provides novel, isolated, tumor-associated antigens, and methods for identifying such antigens in a biological sample, and of screening for the presence of such an antigen in a biological specimen, wherein the tumor antigen identified reacts with serum from a subject treated with a vaccine comprising a cytokine and proliferation-incompetent tumor cells which express the tumor-associated antigen. Also provided are kits for carrying out the methods of the invention.

6 Claims, 15 Drawing Sheets

OTHER PUBLICATIONS

Ganbascher et al., "Interleukin 2 gene transfer into tumor cell abrogates tumorigenicity and induces protective immunity," *J. Exp. Med.*, 172:1217-1224 (1990).

Gansbacher et al., "Retroviral vector-mediated γ-interferon gene transfer into tumor cells generates potent and long lasting antitumor immunity," *Cancer Res.*, 50:7820-7825 (1990).

Gansbacher et al., "Retroviral factors carrying both the IL-2 and the IFN-gamma gene induce potent anti-tumor response in murine tumors," *Proceedings of the American Association for Cancer Research*, 33:351 (1992).

Gerber et al., "Assessment of value of routine bone scans in patients with newly diagnosed prostate cancer," *Urology*, 37:418-422 (1991).

Harlow et al., *Antibodies, A Laboratory Manual*, Cold Spring Harbor Laboratories, 61-67 (1988).

Havell et al., "The antitumor function of tumor necrosis factor (TNF). Therapeutic action of TNF against an established murine sarcoma is indirect, immunologically dependent, and limited by severe toxicity," *J. Exp. Med.*, 167:1067-1085 (1988).

Hersey et al., "Western blot analysis of serological responses following immunization with vaccinia viral lysates of melanoma cells," *Int. J. Cancer*, 46:612-617 (1990).

Hock et al., "Interleukin 7 induces CD4+ T cell-dependent tumor rejection," *J. Exp. Med.*, 174:1291-1298 (1991).

Ikemoto et al., "Clinical stuides on cell-mediated immunity in patients with renal cell carcinoma: interleukin-2 and interferon-γ production of lymphocytes," *Cancer immunology Immunotherapy*, 34:289-293 (1992).

Ioannides et al., "Cytotoxic T-cell clones isolated from ovarian tumour infiltrating lymphocytes recognize common determinants on non-ovarian tumor clones," *Scand J. Immunology*, 37:413-424 (1993).

Koo et al., "Autologues tumor-specific cytotoxicity of tumor-inflitrating lymphocytes derived from human renal cell carcinoma," *J. Immunotherapy*, 10:347-354 (1991).

Lang et al., "Production and response of human prostate cancer cell lines to granulocyte macrophage-colony stimulating factor," *Int J Cancer*, 59:235-241 (1994).

Ley et al., "Interleukin 2-independent activation of tumor-specific cytotoxic T lymphocytes in vivo," *Eur. J. Immunol.*, 21:851-854 (1991).

Nelson et al., "New approaches to adjuvant therapy for patients with adverse histopathologic findings following radical prostatectomy," *The Urologic Clinics of North America*, 23:685-696 (1996).

O'Keefe et al., "Comparative analysis of prostate-specific membrane antigen (PSMA) versus a prostate-specific membrane antigen-like gene," *Prostate*, 58:200-210 (2004).

O'Rourke et al., "Immunotherapy, including gene therapy, for metastatic melanoma," *Aust N Z J. Surg.*, 67:834-841 (1997).

Pardoll, "New strategies for enhancing the immunogenicity of tumors," *Current Opinion in Immunology*, 5:719-725 (1993).

Poehl, "The mail reproductive system: prostatic cell lines," *Atlas of Human Tumor Cell Lines*, Academic Press, Inc., 387-407 (1994).

Porgador et al., "Immunotherapy of tumor metastasis via gene therapy," *Nat. Immun.*, 13:113-130 (1994).

Porgador et al., "Interleukin 6 gene transfection into Lewis lung carcinoma tumor cells suppresses the malignant phenotype and confers immunotherapeutic compentence against parental metastatic cells," *Cancer Res.*, 52:3679-3686 (1992).

Radrizzani et al., "Lysis by interleukin 2-stimulated tumor-infiltrating lymphocytes of autologous and allogeneic tumor target cells," *Cancer Immunol. Immunother.*, 28:67-73 (1989).

Rokhlin et al., "Human prostate carcinoma cell lines secrete GM-CSF and express GM-CSF-receptor on their cell surface," *Anticancer Res.*, 16(2):557-563 (1996).

Sandra et al., "Demonstration of a rational strategy for human prostate cancer gene therapy," *J. Urol.*, 151:622-628 (1994).

Savarese et al., "Expression and function of colony-stimulating factors and their receptors in human prostate carcinoma cell lines," *Prostate*, 34:80-91 (1998).

Simons et al., "Induction of immunity to prostate cancer antigens: results of a clinical trial of vaccination with irradiated autologous prostate tumor cells engineered to secrete granulocyte-macrophage colony-stimulating factor using ex vivo gene transfer," *Cancer Res.*, 59:5160-5168 (1999).

Soiffer et al., "Vaccination with irradiated autologous melanoma cells engineered to secrete human granulocyte-macrophage colony-stimulating factor generates potent antitumor immunity in patients with metastatic melanoma," *Proc. Natl. Acad. Sci. USA.*, 95:13141-13146 (1998).

Spitler, "Cancer vaccines: the interferon analogy," *Cancer Biotherapy*, 10:1-3 (1995).

Tepper et al., "Murine interleukin-4 displays potent anti-tumor activity in vivo," *Cell*, 57:503-512 (1989).

Thomas et al., "Enhanced tumor protection by granulocyte-macrophage colony-stimulating factor expression at the site of an allogeneic vaccine," *Hum. Gene. Ther.*, 9:835-843 (1998).

Urban et al., "Tumor antigens," *Ann. Rev. Immuno.*, 10:617-644 (1992).

van der Bruggen et al., "A gene encoding an antigen recognized by cytolytic T lymphocytes on a human melanoma," *Science*, 254:1643-1647 (1991).

Walczak et al., "Pharmacological treatments for prostate cancer," *Expert Opin Investig Drugs*, 11:1737-1748 (2002) Abstract only.

Watanabe et al., "Exogenous expression of mouse inteferon γ cDNA in mouse neuroblastoma C1300 cells results in reduced tumorigenicity by augmented anti-tumor immunity," *Proc. Natl. Acad. Sci. USA*, 86:9456-9460 (1989).

Wollin et al., "Radiosensitivity of human prostate cancer and malignant melanoma cell lines," *Radiother Oncol.*, 15:285-293 (1989).

* cited by examiner

SEQUENCE LISTING

<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
taaataaata atttttat                                                 18

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
taaataaata a                                                        11

CANCER-ASSOCIATED ANTIGENS AND METHODS OF THEIR IDENTIFICATION AND USE

CROSS-REFERENCE TO RELATED APPLICATIONS

This application is a Continuation of U.S. patent application Ser. No. 11/274,856, filed Nov. 16, 2005, which is a Continuation of U.S. patent application Ser. No. 09/610,891, filed Jul. 6, 2000, which is a continuation of U.S. patent application Ser. No. 09/433,391 filed Nov. 3, 1999 (now abandoned), which claims the priority benefit of U.S. Provisional Patent Application No. 60/106,795, filed Nov. 3, 1998, each of which is incorporated by reference herein in it's entirety.

FIELD OF THE INVENTION

The present invention relates generally to the fields of cancer diagnosis and therapy. More particularly, the present invention relates to novel, isolated, tumor-associated antigens not previously recognized by the immune system of a patient with cancer, methods of identifying such antigens, and methods of utilizing such antigens to treat primary and metastatic neoplasms. This invention also relates to screening methodologies for identifying those individuals diagnosed with conditions characterized by the expression of these tumor-associated antigens.

BACKGROUND OF THE INVENTION

The immune system plays a critical role in the pathogenesis of neoplasia. The shortcomings of the immune system in this disorder can be broadly considered as the failure to develop a sufficiently potent response to a deleterious target. Standard medical treatments for cancer, including chemotherapy, surgery, and radiation therapy, have clear limitations with regard to both efficiency and toxicity. While prevention of primary and/or metastatic cancer would be ideal, these approaches typically have met with little success. New strategies which stimulate the immune system to mount a successful attack on neoplastic cells are greatly needed.

It is known that the presence of a neoplasm may elicit a cellular immune response. For example, blood and tumor infiltrates from melanoma and renal carcinoma patients contain circulating cytotoxic precursor cells with specific reactivity for autologous melanoma (see, e.g., Darrow et al. (1989) *J. Immunol.* 142:3329-35; Crowley et al. (1991) *J. Immunol.* 146:1692-9; Crowley et al. (1992) *Cancer Res.* 52:394) and renal carcinomas (see, e.g., Belldegrun et al. (1988) *Cancer Res.* 42:206-214; Radrizzani et al. (1989) *Cancer Immunol. Immunother.* 28:671; Belldegrun et al. (1990) *Cancer Immunol. Immunother.* 31:1; Ikemoto et al. (1992) *Cancer Immunol. Immunother.* 34:289; Koo et al. (1991) *J. Immunol. Ther.* 10:347; Alexander et al. (1990) *J. Cancer.* 45:119). This cellular response may result from the presence of tumor rejection antigens on the surface of tumor cells (see, e.g., U.S. Pat. No. 5,763,155). However, a serological response to the tumor has been difficult to demonstrate.

Several hypotheses for this inability exist, such as that tumor cells are poor antigen-presenting cells, have low or absent MHC molecules expressed on the cell surface, secrete suppressor factors, or that T-cell receptor (TCR) engagement by the tumor antigens without a costimulatory signal induces anergy. The inability of the immune system to elicit an antibody response may also or alternatively result, in part, from the inability of the immune system to distinguish a neoplastic cell from a normal, non-cancerous cell due to the possession of common surface antigens.

Immunotherapy for cancer is based on the premise that the immune system can be activated or manipulated to recognize and eradicate tumors. Systemic immune responses to tumor cells have been shown to be capable of mediating tumor rejection in animal models and in some patients with cancer (Joannides, et al. (1993) *Immunol.* 37:413-442; Urban et al. (1993) *Ann. Rev. Immunol.* 10:617-644; Van der Bruggen, et al. (1991) *Science* 254:1643-1647; Porgador, et al. (1994) *Nat. Immunol.* 13:113-130; and Pardoll (1993) *Curr. Op. Immunol.* 5:719-725).

Approaches to activate the immune system have included the use of vaccines. A vaccine is a way of delivering an antigen to the immune system such that the immune system recognizes the antigen as foreign and rejects or destroys any cells bearing that antigen. Proliferation-incompetent allogeneic or autologous tumor cells have been used as vaccines. For example, polyvalent allogeneic melanoma vaccines have been reported to improve survival of patients with metastatic melanoma (Sanda et al. (1994) *J. Urol.* 151:622-628). In addition, vaccines derived from allogeneic melanoma tumor cell lines have not been associated with clinically significant toxicity when given alone (Dranoff et al. (1993) *Proc. Natl. Acad. Sci.* (USA) 90:35-39). However, such immunity has been short-lived.

Autologous cancer cells also have been used as vaccines to augment anti-tumor immunity (Oettgen et al. in *Biologic Therapy of Cancer* (1991), Devita et al., eds., 5 Lippincott Co., pp. 87-119). Such vaccines, in theory, should be very powerful because they are highly specific for the tumor from which the vaccine was prepared. However, the immunogenicity of cancer cells is generally too weak to elicit a pronounced immune reaction sufficient to overcome the disease, perhaps due to the theories described above. Patient responses to these "raw" vaccines have generally been only partial and relatively short lived. Thus, methods of increasing the immune system recognition of and response to neoplastic cells are greatly needed.

One strategy to improve the efficacy of such vaccinations has included the use of non-specific adjuvants or immunostimulants such as BCG and *Corynebacterium parvum*. However, this has resulted in little improvement.

Another approach has been to increase the immunogenicity of tumor cells by treating the cells to be injected in different ways to enhance the exposure of their surface antigens. For example, U.S. Pat. No. 4,931,275 describes, using as a vaccine, cells treated with pressure or cholesteryl hemisuccinate, or using as vaccines plasma membranes or membrane proteins from these cells.

Another approach has focused on the interaction of cytokines and the immune system. Cytokines and combinations of cytokines have been shown to play an important role in the stimulation of the immune system. For example, U.S. Pat. No. 5,098,702, describes using combinations of TNF, IL-2 and IFN-β in synergistically effective amounts to combat existing tumors. U.S. Pat. No. 5,078,996 describes the activation of macrophage nonspecific tumoricidal activity by injecting recombinant GM-CSF to treat patients with tumors. However, because the doses of cytokines necessary to effect tumor development are often systemically toxic, direct treatment of patients is frequently not feasible (see, e.g., Asher et al., (1991) *J. Immun.* 146:3227-3234 and Havell et al., (1988) *J. Exp. Med.* 167:1067-1085).

To avoid such toxicity, non-neoplastic cells genetically modified to express a cytokine have been administered as vaccines. For example, autologous fibroblasts genetically modified to secrete IL-2 have been administered with a tumor antigen at a site other than an active tumor site. In a related approach, the fibroblast has been genetically modified to express both a cytokine and the tumor antigen (see, e.g., U.S. Pat. No. 5,674,486 Sobel, et al.).

In an alternative approach, tumor cells, themselves, have been genetically modified to express a cytokine. These vaccines have been used to potentiate tumor-associated antigen presentation to T cells of a subject. For example, studies have shown that the introduction of cytokine genes into murine tumor cells induced increased immunogenicity and decreased tumorigenesis (see, e.g., Gansbacher et al., (1990) *Cancer Res.* 50: 7820-7825; Fearon et al., (1990) *Cell.* 60:397-403; Ley et al., (1981) *Eur. J. Immunol.* 21:851-854; Watanabe et al., (1989) *Proc. Natl. Acad. Sci.* (USA) 86:9456; Gansbacher et al., (1990) *J. Exp. Med.* 172:1217-1224; Gansbacher et al., (1992) *Proc. Am. Assoc. Cancer Res.* 33:351; Tepper et al., (1989) *Cell* 57:503-512; Hock et al., (1991) *J. Exp. Med.* 174:1291-1298; and Porgador et al., (1992) *Cancer Res.* 52:3679). In addition, localized high concentrations of certain cytokines delivered by genetically modified cells have led to tumor regression in animals and humans (see, e.g., Gansbacher et al., (1990) *Cancer Res.*, 50:7820-7825; Fornis et al., (1988) *Cancer Met. Rev.*, 7:289-309; Fearon et al., (1990) *Cell* 60:397-403; and published GVAX® vaccine patent applications and patents), and in some cases, tumor immunity (Fearon et al., (1990) *Cell* 60:397-403). Thus, activating the immune system to respond to a tumor is a viable therapeutic alternative to irradiation and chemotherapy. Accordingly, improved, more efficacious activation methods specific for certain cancers are greatly needed.

One method of activating the immune system is to identify novel tumor-associated antigens such as tumor rejection antigens. U.S. Pat. No. 5,763,155 describes the identification of the MACE oncofetal family of tumor rejection antigens which are melanoma-associated. These antigens are recognized by host human T cells, but may not elicit an antibody response. Unfortunately, clinically relevant tumor rejection antigens for immune therapy for the treatment of most other types of cancer have not yet been identified.

Thus, the identification of clinically relevant, tumor-associated antigens is needed to provide improved methodologies for stimulating the immune system to recognize a tumor cell not normally targeted such that the tumor cell will elicit an effective cellular and serological or humoral response. Also needed are methods of screening for such antigens.

SUMMARY OF THE INVENTION

It has been discovered that particular tumor-associated antigens expressed by neoplastic and some normal cells are recognized by the immune system of human cancer patients after treatment with tumor cells which express certain cytokines. This discovery has been exploited to develop the present invention, which includes novel, isolated, tumor-associated antigens and methods of their identification and use.

More particularly, in a first aspect, the present invention provides a method for identifying a tumor-associated antigen. These tumor-associated antigens are cancer-associated and may also be tissue-specific. As used herein, the term "tumor-associated" refers to an antigen which is found on or expressed by a tumor cell, but which also may be found on or expressed by other non-cancerous cells, for example, at over-expressed or developmentally untimely levels. A "tumor-associated antigen" encompasses solid tumors and liquid tumors such as ascites fluid produced by ovarian cancer, pleural effusion produced by lung carcinomas, and nonsolid hematologic tumors. The term "tissue-specific" refers to an antigen which is found mainly on a particular tissue type.

In the identification method of the present invention, an array of proteins is prepared from a biological sample. In some embodiments, the biological sample is blood, serum, a tissue biopsy, spinal fluid, saliva, lacrimal secretions, semen, vaginal secretions, feces, urine, ascites fluid, or a tumor cell line. In preferred embodiments, the biological sample is serum or blood. In other embodiments, the biological sample is a tumor cell line. In particular embodiments, the array is prepared by separating the proteins by molecular weight. In some embodiments, the proteins are separated by sodium dodecyl sulfate-polyacrylamide gel electrophoresis (SDS-PAGE).

A first serum sample and a second serum sample are obtained from a subject, respectively, before and after treatment of the subject with a vaccine comprising an immune system potentiator and/or enhancer and proliferation-incompetent tumor cells which express the tumor-associated antigen. A first sample of the array of proteins is contacted with the first serum sample, and a second sample of the array of proteins is contacted with the second serum sample. A protein is then identified in the array which reacts with the second serum sample but not with the first serum sample, the reactive protein being a tumor-associated antigen which elicited an immune response by the subject after treatment of the subject with the vaccine.

As used herein, the term "proliferation-incompetent" refers to cells which are unable to divide, but which express genes which encode tumor-associated proteins. In a particular embodiment, the serum samples are purified so as to remove components that are not antibodies before they are used to contact the protein arrays.

The term "immune system potentiator and/or enhancer" is used herein to encompass any protein-based molecule which is involved with the initiation, enhancement, strengthening, heightening, and/or lengthening of an immune response. In some embodiments, the potentiator and/or enhancer is GM-CSF, IL-1, IL-3, IL-4, IL-6, IL-7, IL-10, CD2, IL-12, IL-15, IL-18, TGF-β, B7, MIP-1α, MIP-1β, MIP-2, M-CSF, G-CSF, and/or ICAM. The immune system potentiator and/or enhancer is a cytokine in some embodiments, and in a preferred embodiment, the cytokine is granulocyte-macrophage colony stimulating factor (GM-CSF). In other embodiments, the vaccine further comprises at least two immune system potentiators and/or enhancers. In a particular embodiment, the proliferation-incompetent tumor cells have been genetically engineered to express the immune system potentiator and/or enhancer. In a particular embodiment, the tumor cells have been genetically engineered to express GM-CSF. In other embodiments the immune system potentiator and/or enhancer is expressed by a non-tumor cell. In one embodiment, a non-tumor cell has been genetically engineered to express the immune system potentiator/enhancer.

In some embodiments, the tumor cells are autologous tumor cells. An "autologous tumor cell" is one obtained from a tumor found in the patient, or is a primary descendent of such a cell. In other embodiments, the tumor cells are allogeneic. An "allogeneic tumor cell" is a tumor cell of the same type as that being harbored by the subject but is derived from an established tumor cell line derived from an unrelated subject, or alternatively, is a tumor derived cell originating from an unrelated tumor type but sharing common tumor-associated antigens.

In one embodiment, the subject is a mammal. In preferred embodiments, the subject is human harboring a neoplasm. In particular embodiments of the invention, the subject is a human subject and the biological sample and the tumor cells are of human origin. In one embodiment, the human subject has prostate cancer and the tumor cells are from one or more prostate tumor cell lines. In another embodiment, the human subject has colon cancer and the tumor cells are from one or more colon cancer tumor cell lines. In yet another embodiment, the human subject has breast cancer and the tumor cells are from one or more breast cancer cell lines. In still another embodiment, the human subject has ovarian cancer and the tumor cells are from one or more ovarian cancer tumor cell lines.

In another aspect, the invention provides a method of screening for the presence of a tumor-associated antigen in a biological specimen. In this method, a tumor-associated antigen identified as described above is isolated. An antibody directed to the tumor-associated antigen is prepared, the tumor-associated antigen being reactive with the serum of a subject treated with a vaccine comprising an immune system potentiator and/or enhancer and proliferation-incompetent tumor cells which express the tumor-associated antigen, and not being reactive with the serum of the untreated subject. The biological specimen is then contacted with the antibody. A detection is made of whether there is an antigen-antibody reaction, the presence of such a reaction being indicative of the presence of the tumor-associated antigen in the tissue specimen, and the absence of such a reaction being indicative of no tumor-associated antigen being present. In some embodiments, the tumor-associated antigen in the biological specimen is on a tumor cell. In one embodiment, the antibody is a monoclonal antibody. In another embodiment, the antibody comprises polyclonal antibodies. In some embodiments, the biological specimen is blood, serum, a tissue biopsy, spinal fluid, saliva, lacrimal secretions, semen, vaginal secretions, feces, urine, ascites fluid, or a tumor cell line.

In one embodiment, the specimen is taken from a subject with carcinoma and the antibody is directed to a tumor-associated antigen having a molecular weight of about 150 kD as determined by SDS-PAGE. In a some embodiments, the specimen is taken from a subject with prostate carcinoma, breast carcinoma, lung carcinoma, colon carcinoma, ovarian cancer, or leukemia.

The invention also provides isolated, tumor-associated antigens. In some embodiments, the novel, isolated tumor-associated antigens have molecular weights of about 250 kD, 160 kD, 150 kD, 130 kD, 105 kD, 60 kD, 32 kD, 31 kD, 27 kD, 26 kD, 14 kD, and 12 kD, as determined by SDS-PAGE, and do not cross-react immunologically with prostate specific antigen (PSA). It is understood that the fact that a tumor-associated antigen does not cross-react with PSA becomes important where the serum is from a prostate cancer patient that may be expressing PSA. In one embodiment of the invention, the antigen is carcinoma-associated and has a molecular weight of about 150 kD as determined by SDS-PAGE.

Other aspects of the present invention include improved vaccines and methods for treating cancer. In one embodiment, the vaccine comprises a naked nucleic acid encoding at least one tumor-associated antigen of the invention which is not tumorigenic. In some embodiments, the nucleic acid is RNA or DNA, which may be genomic DNA or cDNA. In other embodiments, the vaccine comprises the tumor-antigen-encoding DNA linked to lipids or encased within a liposome. In some embodiments, the vaccine further comprises a nucleic acid encoding at least one immune system potentiator and/or enhancer. In one embodiment, the potentiator and/or enhancer is a cytokine. In a preferred embodiment, the cytokine is GM-CSF. In some embodiments, the nucleic acid is RNA or DNA, which may be genomic DNA or cDNA.

In an alternative embodiment, the vaccine comprises a vector encoding both a cytokine and a novel tumor-associated antigen of the invention, the antigen itself being non-tumorigenic. In some embodiments, the vector is a viral vector. In particular embodiments, the viral vector is an adenoviral vector, adeno-associated viral vector, lentiviral vector, sindbis viral vector, retroviral vector, herpesviral vector, SV-40 vector, or a pox viral vector such as a vaccinia viral vector. In preferred embodiments, the cytokine is GM-CSF. In some embodiments, the vector encodes more than one cytokine and/or tumor antigen, and/or includes more than one copy of the same cytokine gene or tumor-associated antigen gene. The vector alternatively encodes at least an antigenic or immunogenic portion of the tumor-associated antigen in some embodiments of the invention.

In another aspect, a vaccine is provided which comprises a tumor-associated antigen of the invention. In some embodiments, the vaccine further comprises an immune system potentiator and/or enhancer. In some embodiments, this may be a cytokine. In particular embodiments, the vaccine comprises GM-CSF, IL-1, IL-3, IL-4, IL-6, IL-7, IL-10, CD2, IL-12, IL-15, IL-18, TGF-β, B7, MIP-1α, MIP-1β, MIP-2, M-CSF, G-CSF, and/or ICAM. In a preferred embodiment, the cytokine is GM-CSF.

In yet another embodiment, the invention provides a cell-based vaccine which comprises proliferation-incompetent tumor cells expressing a tumor-associated antigen of the invention. The vaccine further comprises an immune system potentiator and/or enhancer. In particular embodiments, the vaccine further comprises GM-CSF, IL-1, IL-3, IL-4, IL-6, IL-7, IL-10, CD2, IL-12, IL-15, IL-18, TGF-β, B7, MIP-1α, MIP-1β, MIP-2, M-CSF, G-CSF, and/or ICAM. In some embodiments, the vaccine further comprises a cytokine. In a preferred embodiment, the cytokine is GM-CSF. In some embodiments, the tumor cell expresses the potentiator and/or enhancer. In other embodiments, a normal cell expresses the potentiator and/or enhancer.

In particular embodiments, the nucleic acid-, vector-, protein-, and cell-based vaccines of the invention further comprise an adjuvant and/or a helper cell such as an untransformed, proliferation-incompetent tumor cell or a non-neoplastic cell which enhances or potentiates the immunogenic response.

In another aspect, the invention provides a method of treating cancer comprising the administration of a vaccine of the invention to a cancer patient in a therapeutically effective amount. A "therapeutically effective amount" of the vaccine is that amount which elicits an immune response to the patient's tumor cells such that the tumor or neoplastic lesion in the patient decreases in size, the patient goes into remission, and/or metastatic cells are destroyed.

The invention, in another aspect, provides a vector containing RNA, DNA, genomic or cDNA, encoding a cytokine and a tumor-associated antigen or immunogenic portion thereof. In some embodiments, the vector is a viral vector such as a retroviral vector, an adenoviral vector, an adeno-associated viral vector, a herpesviral vector, an SV-40 viral vector, a lentiviral vector, a sindbis viral vector, or a pox viral vector such as a vaccinia viral vector. In a preferred embodiment, the cytokine that is encoded is GM-CSF.

The invention also provides a cell transduced with nucleic acid encoding a novel tumor-associated antigen or multiple tumor-associated antigens as well as a cytokine. In some embodiments, the cytokine encoded is GM-CSF, and in some embodiments, the novel tumor-associated antigen is carcinoma-associated and has a molecular weight of about 150 kD. In other embodiments, the novel, isolated tumor-associated antigen has a molecular weight of about 250 kD, 160 kD, 130 kD, 105 kD, 60 kD, 32 kD, 31 kD, 27 kD, 26 kD, 14 kD, or 12 kD.

In yet another aspect, the invention provides a method of preventing cancer in a subject by administering one or more of the vaccines of the invention. In some embodiments, the vaccine is delivered to the subject intramuscularly, intradermally, or subcutaneously.

In other aspects, the invention provides polyclonal and monoclonal antibodies reactive with novel tumor-associated antigens or cells transduced with DNA encoding a cytokine and expressing at least an immunogenic portion of a novel tumor-associated antigen.

In yet another aspect, the invention provides a kit for screening for the presence of a tumor-associated antigen in a biological sample. The kit comprises unlabelled first antibodies directed to a tumor-associated antigen, the tumor-associated antigen being reactive with serum from a subject treated with a vaccine comprising proliferation-incompetent tumor cells which express the tumor-associated antigen and GM-CSF, but not being reactive with serum from the subject before treatment with the vaccine. The kit also comprises a solid support for adhering the first antibodies directed to the tumor-associated antigen. In one embodiment, the solid support is plastic. Additionally, the kit includes labelled second antibodies. In some embodiments, the first and second antibodies are monoclonal antibodies. In a certain embodiment, the unlabelled first antibody is a monoclonal antibody directed to a first epitope of the tumor-associated antigen, and the labelled second antibody is a monoclonal antibody directed to a different epitope of the tumor-associated antigen. In a particular embodiment, the first and second antibodies are human antibodies. In some embodiments, the second antibody is labelled with a radioactive compound, enzyme, or dye.

In still another aspect, the invention provides a kit for screening for the presence of a tumor-associated antigen in a biological sample. The kit comprises unlabelled first antibodies directed to a tumor-associated antigen, the tumor-associated antigen being reactive with serum from a subject treated with a vaccine comprising proliferation-incompetent tumor cells which express the tumor-associated antigen and GM-CSF and, but not being reactive with serum from the subject before treatment with the vaccine. The kit also comprises a solid support for adhering the biological sample thereto, the sample possibly containing a tumor-associated antigen. In one embodiment, the solid support is plastic. Additionally, the kit includes labelled second antibodies directed to the first antibodies. In some embodiments, the first and second antibodies are monoclonal antibodies. In a particular embodiment, the first and second antibodies are human antibodies. In some embodiments, the second antibodies are labelled with a radioactive compound, enzyme, or dye.

DESCRIPTION OF THE DRAWINGS

The foregoing and other objects of the present invention, the various features thereof, as well as the invention itself, may be more fully understood from the following description, when read together with the accompanying drawings, in which.

Figure 7:
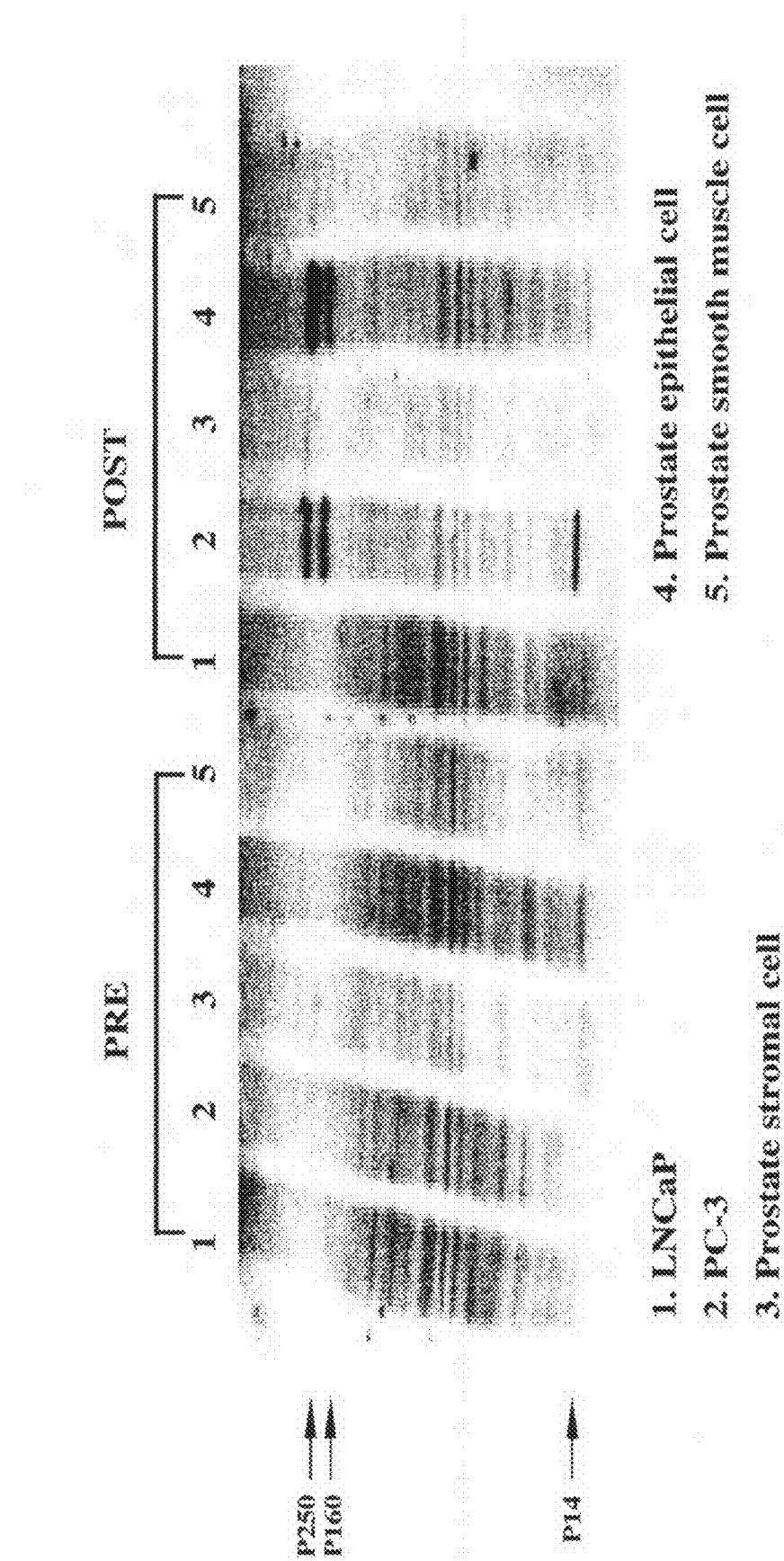
Figure 8A:
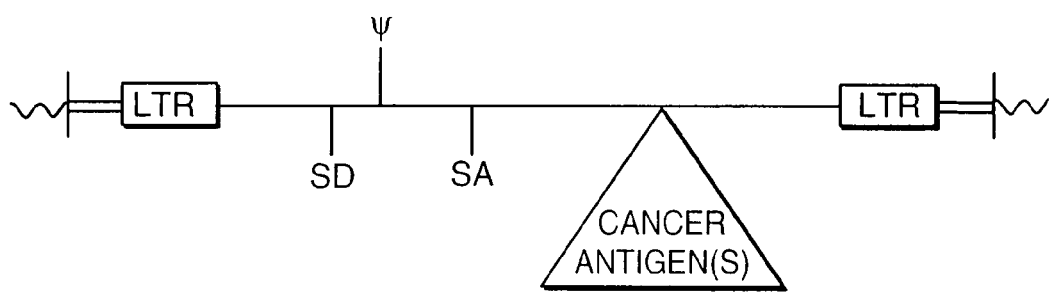
Figure 8B:
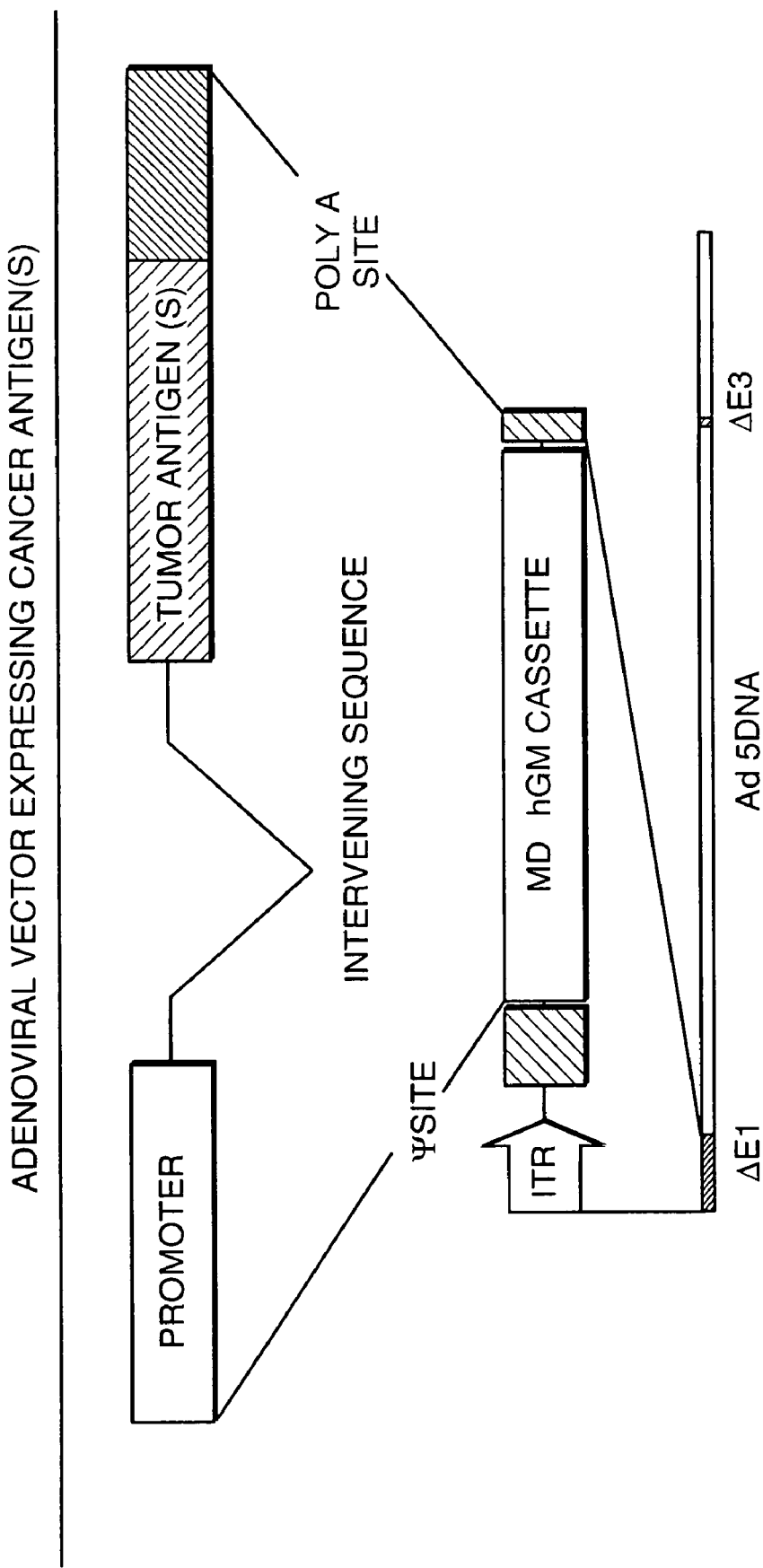

LS-174T (colon carcinoma); (5) MCF7 breast carcinoma; (6) DU-145 (prostate carcinoma); (7) KLEB (ovarian cancer); (8) Jurkat (leukemia); and (8) MDA-435S (breast carcinoma);

FIG. 7 is a representation of a Western blot in which the expression of the p250, p160, and p14 antigens was examined using the sera from an allogeneic GVAX® vaccine treated patient on the following cell lines: (1) LNCaP prostate cancer cell line; (2) PC-3 prostate carcinoma; (3) normal prostate stroma; (4) normal prostate epithelial; and (5) normal prostate smooth muscle;

FIG. 8A is a schematic representation of a retroviral vector encoding GM-CSF and one or more tumor-associated antigens of the invention; and FIG. 8B is a schematic representation of an adenoviral vector encoding GM-CSF and one or more tumor-associated antigens of the invention.

DETAILED DESCRIPTION OF THE INVENTION

The patent and scientific literature referred to herein establishes the knowledge that is available to those with skill in the art. The issued U.S. patents, allowed applications, published foreign applications, and references cited herein are hereby incorporated by reference.

The present invention discloses clinically relevant, novel, isolated, tumor-associated antigens which become identifiable in an antigen-antibody binding assay by the sera of patients treated with the GVAX® vaccine. These tumor-associated antigens may be expressed by a primary or metastatic tumor cell, and/or by some non-tumor cells in an overexpressed or untimely fashion), alike. Prior to GVAX® vaccine treatment, these antigens may not be, or are weakly, immunogenic despite the fact that they may be overexpressed on neoplastic cells. GVAX® vaccine treatment enables the immune system of the patient to recognize the antigen, thereby overcoming immune tolerance to the antigen that existed before treatment. The immune responses induced by the antigen may suppress tumor growth, lead to eradication of the tumor, and/or may be the useful markers for disease diagnosis.

Accordingly, the present invention provides a method of identifying tumor-associated antigens. In this method an array of proteins is prepared from a biological sample. A first serum sample and a second serum sample are obtained from a subject, respectively, before and after treatment of the subject with the GVAX®-type vaccine described above. A first sample of the array of proteins is contacted with the first serum sample, and a second sample of the array of proteins is contacted with the second serum sample. A protein in the array which reacts with the second serum sample but not with the first serum sample is then identified, the reactive protein being a tumor-associated antigen which elicited an immune response by the subject after treatment of the subject with the GVAX® vaccine.

As described above, it is the GVAX® vaccine treatment which enables identification of the novel tumor-associated antigens. In this treatment, patients harboring a tumor are immunized with tumor cell-based vaccines that cause the immune system to be activated against antigens expressed by the tumor. These antigens are likely to be comprised of normal tissue antigens, new, mutated, tumor-specific antigens, or oncofetal antigens. The predominance of normal self antigens expressed by tumors has been well documented. As these are normal "self" antigens, the patient's immune system is already tolerized to them. With GVAX® vaccine treatment, immunization overcomes tolerance to self antigens.

GVAX® vaccine treatment begins with immunization of a patient with cancer cells that have been rendered proliferation-incompetent and have been genetically engineered to express the cytokine, GM-CSF. Other cytokines and other immune system potentiators and/or enhancers are useful in the vaccine in place of, or in addition to, GM-CSF. The tumor cell may be genetically engineered to express the cytokine by any known method of gene transfer. An example of such method includes the use of a vector encoding the cytokine, such as a viral vector. Any viral vector capable of infecting the cell may be used including, but not limited to, retroviral vectors, adenoviral vectors, adeno-associated viral vectors, lentiviral vectors, sindbis viral vectors, herpesviral vectors, SV-40 vectors, and pox viral vectors, such as vaccinia (see, e.g., U.S. Ser. No. 90/324,707).

For example, a variety of retroviral vectors may be used. The MFG, α-SGC, pLJ, and pEm, and derivatives thereof, (FIGS. 1A-1D) are more fully disclosed in U.S. Ser. No. 07/786,015, filed Oct. 31, 1991 (PCT/US91/08121, filed Oct. 31, 1991), incorporated herein by reference. One format of the GVAX® vaccine utilizes a single infection of a tumor cell by a retroviral vector encoding one or more cytokines which may be of the same or different type. In an alternative format of the GVAX® vaccine, multiple infections by multiple retroviral vectors encoding different cytokines are utilized.

Figure 1A:
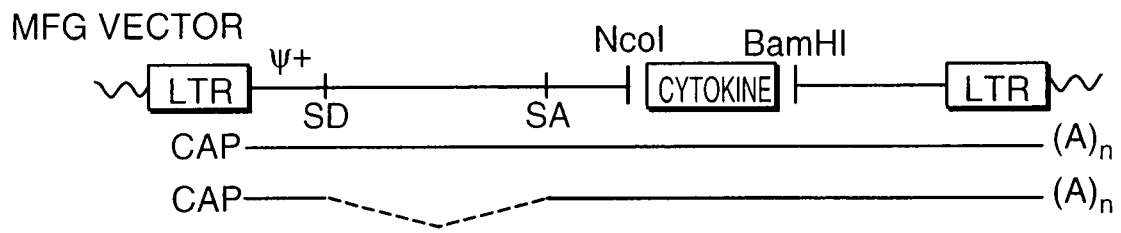
FIG. 1A is a schematic representation of the MFG vector containing a cytokine-encoding sequence useful in the methods and vaccines of the present invention.
Figure 1B:
FIG. 1B is a schematic representation of the pLJ vector useful in methods and vaccines of the present invention, wherein the "∇" represents the insertion of the nucleic acid sequence encoding the cytokine.
Figure 1C:
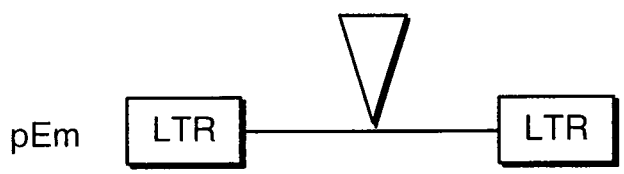
FIG. 1C is a schematic representation of the pEm vector useful in methods and vaccines of the present invention, wherein the "∇" represents the insertion of the nucleic acid sequence encoding the cytokine.
Figure 1D:
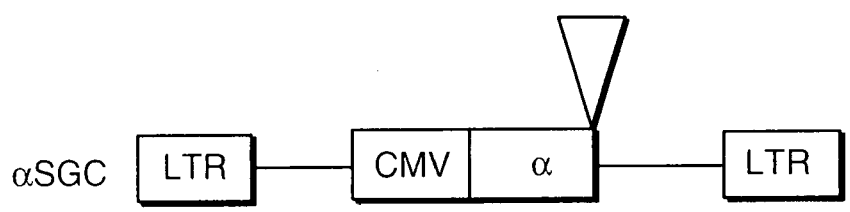
FIG. 1D is a schematic representation of the α-SGC vector useful in methods and vaccines of the present invention, wherein the "∇" represents the insertion of the nucleic acid sequence encoding the cytokine.
Figure 1E:
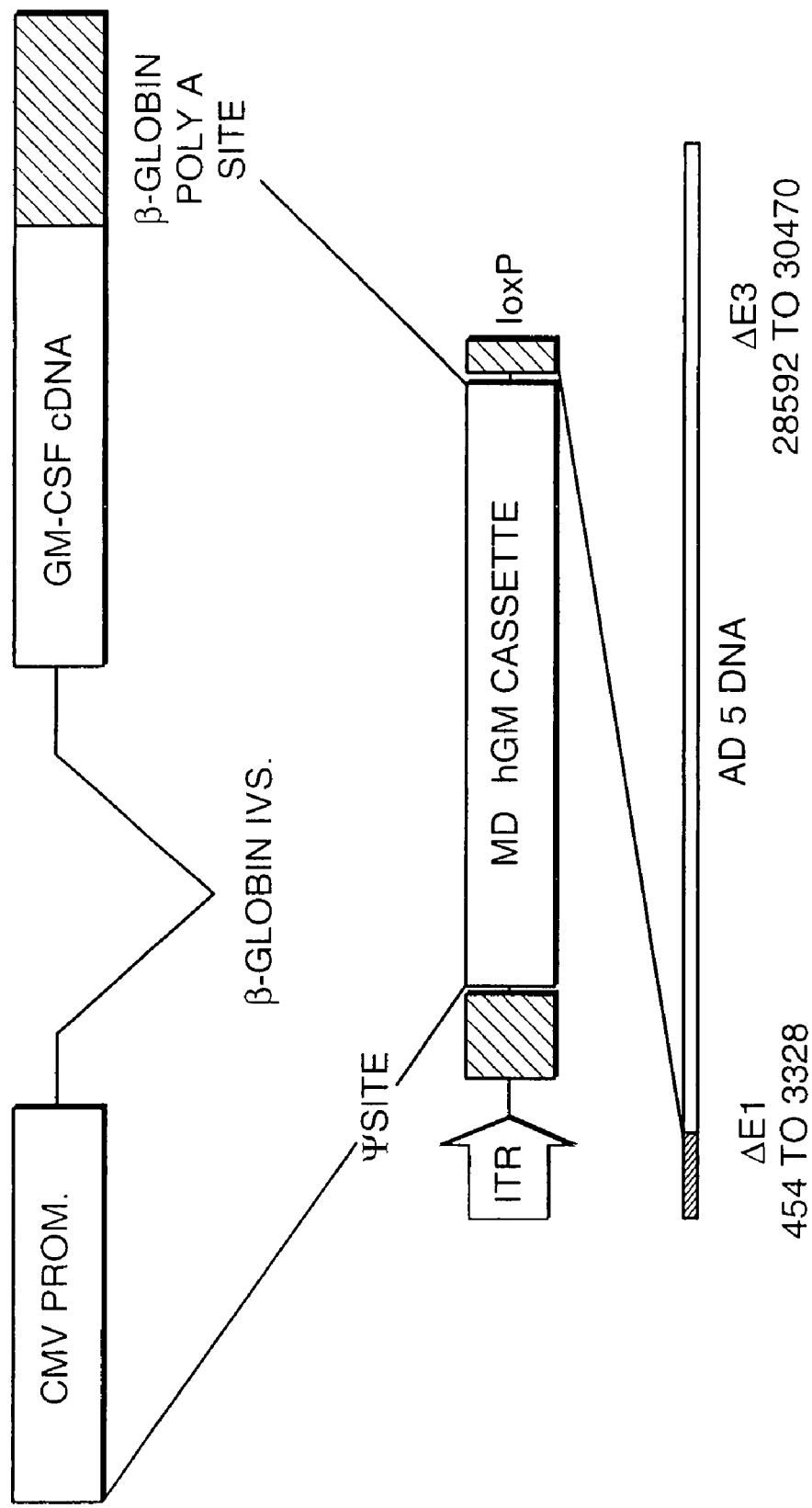
FIG. 1E is a schematic representation of a GM-CSF-encoding adenovirus vector (AV-GM-CSF) useful in methods and vaccines of the present invention.
Figure 1F:
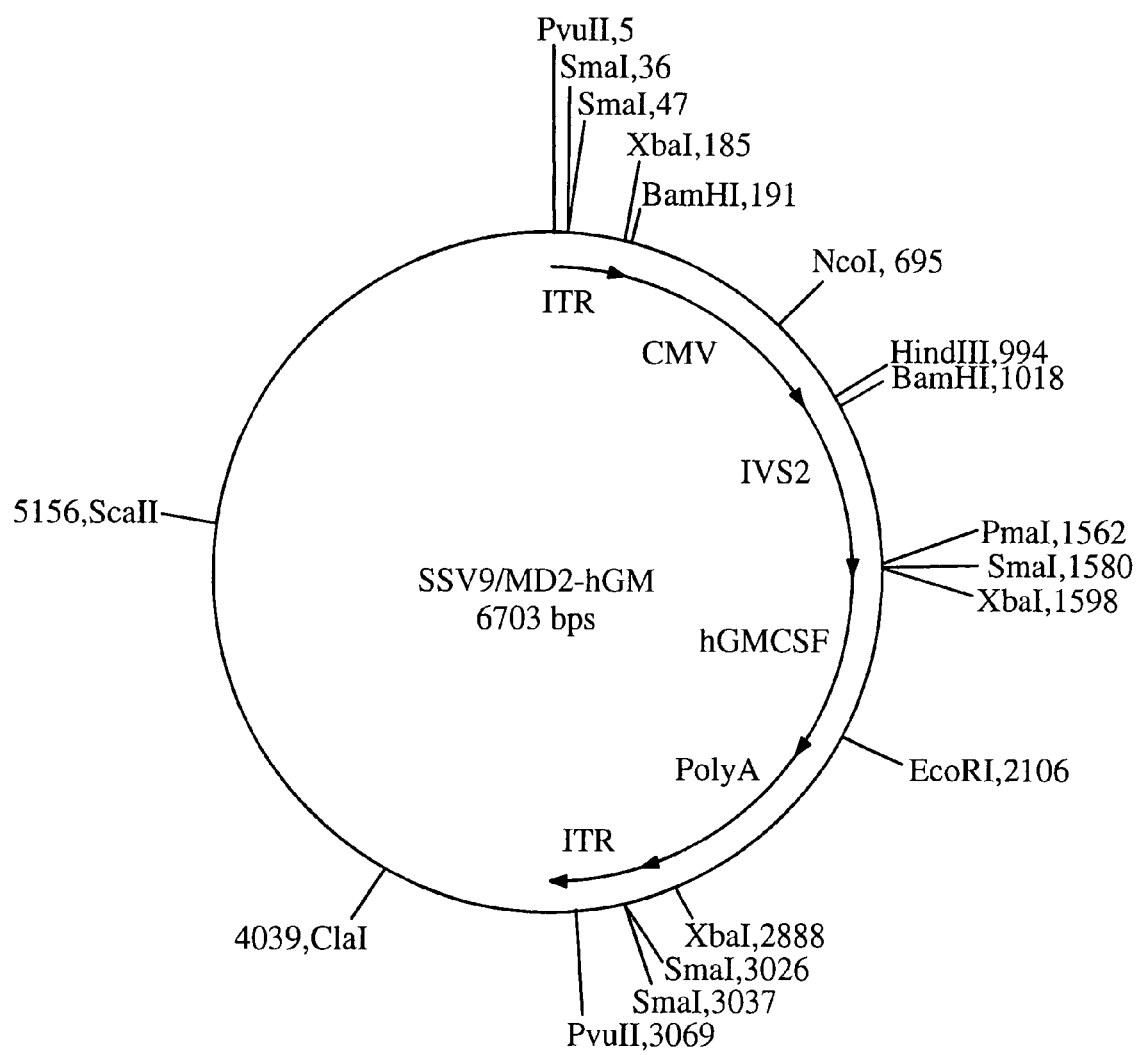
FIG. 1F is a schematic representation of a recombinant adeno-associated viral (AAV) vector plasmid (SSV9/MD2-hGM) useful in methods and vaccines of the present invention.
Figure 1G:
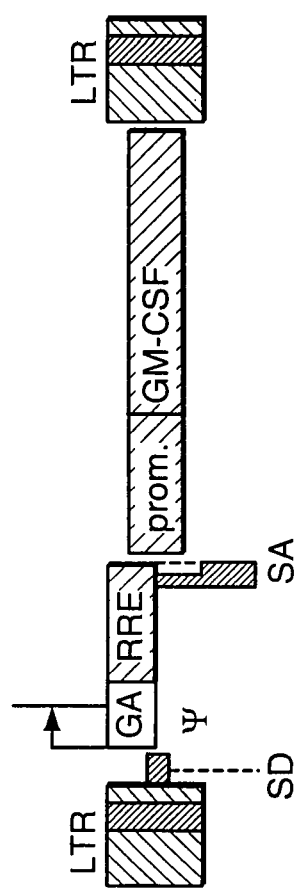
FIG. 1G is a schematic representation of a recombinant lentivirus vector containing a GM-CSF expression cassette flanked by HIV LTRs, useful in the methods and vaccines of the present invention.
Figure 1H:
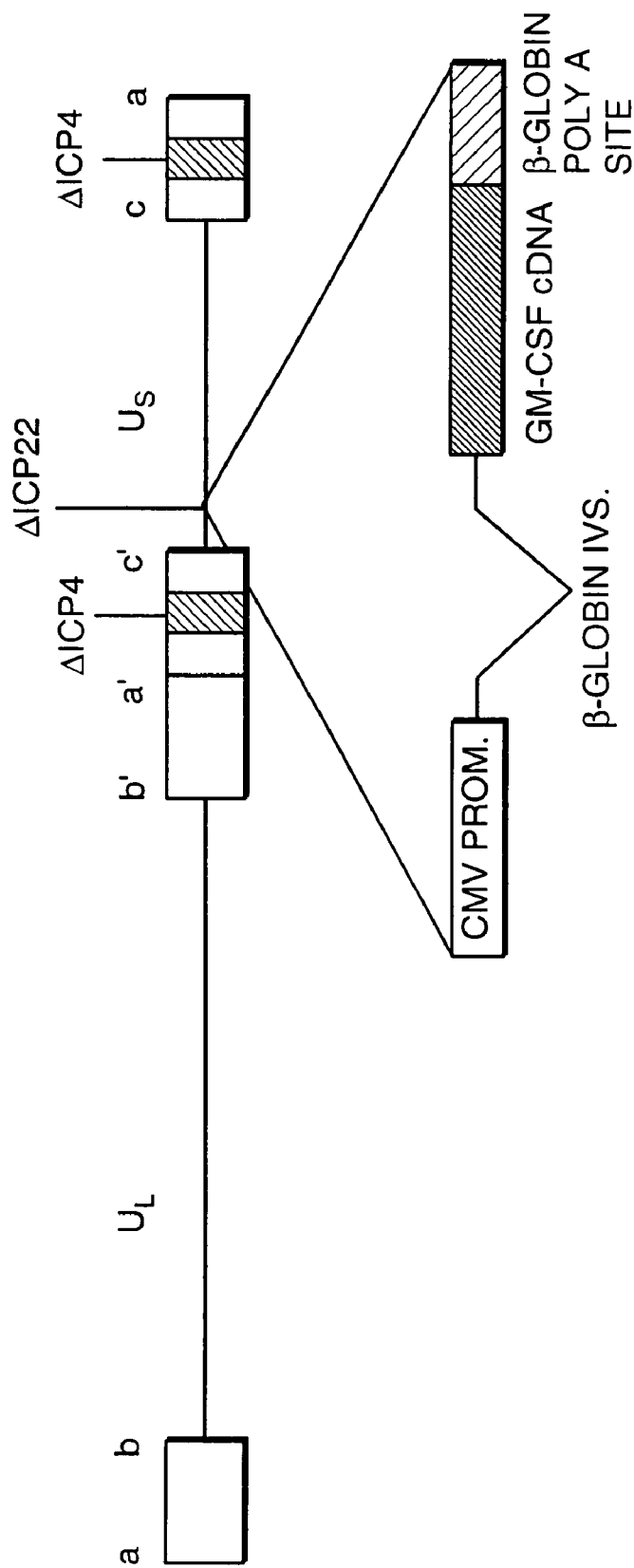
FIG. 1H is a schematic representation of an HSV-1-based vector containing a GM-CSF expression cassette replacing the ICP22 HSV gene, useful in the methods and vaccines of the present invention.
Figure 1I:
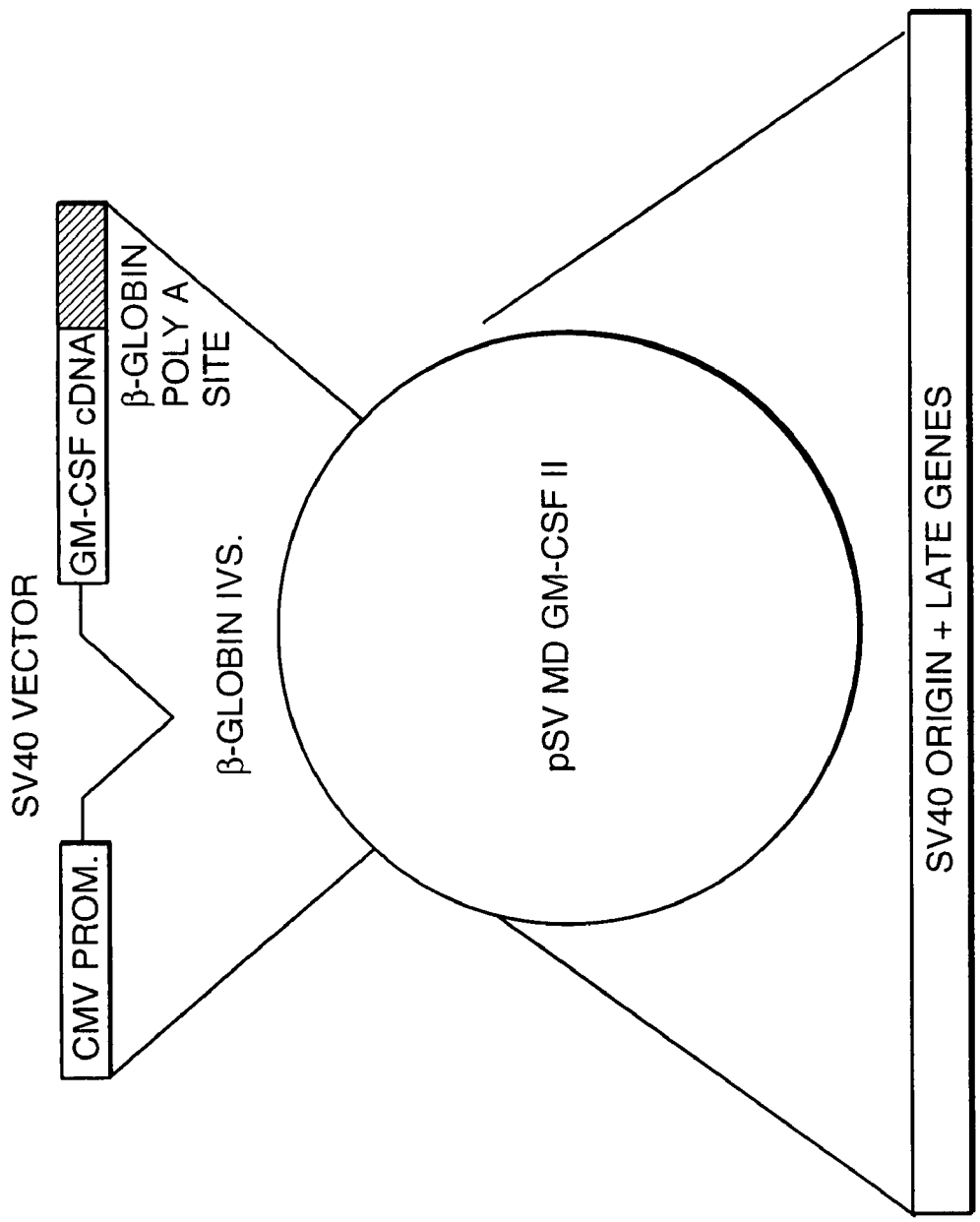
FIG. 1I is a schematic representation of an SV-40-based plasmid (pSV HD GM-CSFII) including a GM-CSF expression cassette, the SV-40 origin of replication, and viral late genes, useful in the methods and vaccines of the present invention.
Figure 1J:
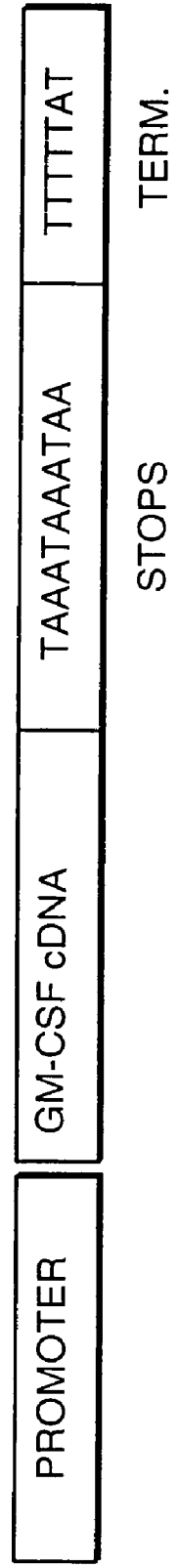
FIG. 1J is a schematic representation of a vaccinia virus expression cassette including a vaccinia virus promoter and termination sequence, useful in the methods and vaccines of the present invention.

Other viral vectors may be used to transduce the tumor cell of the GVAX® vaccine. For example, particularly useful viral vectors are those capable of infecting mammalian cells which are not replicating, or quiescent, allowing for efficient transduction of cells without the necessity of cell culture. One such viral vector is constructed from an adenovirus, a representative example of which is shown in FIG. 1E. Other viral vectors useful in the GVAX® vaccine methods of the invention include, but are not limited to, an adeno-associated viral (AAV) vector, lentivirus vectors, sindbis viral vectors, herpesvirus vectors, SV-40 virus vectors, and a pox virus vector such as, but not limited to, a vaccinia virus vector (see FIGS. 1F-1J for representative examples). The GVAX® vaccine may utilize a single infection of a tumor cell by one or more of these vector(s) encoding at least one cytokine, or it may utilize multiple infections by such vectors encoding different cytokines.

One of ordinary skill will realize that the above vectors may be subtly altered in a manner such that the operative features, vis-a-vis transduction efficacy, are substantially maintained. As such, the present invention also contemplates the use of any and all operative (transduction-competent) derivatives of the above retroviral, adenoviral, adeno-associated viral, lentiviral, sindbis viral, SV-40, herpesviral and pox viral constructs to deliver genes encoding immunomodulatory agents to cells. For example, the retroviral vector MFG-S comprises three point mutations in the MFG vector which theoretically improve the safety of the vector (although there is no evidence that MFG is unsafe) while retaining substantially identical transfection efficiency. Specifically, MFG-S has an A to T change at nucleotide 1256, a C to T mutation at nucleotide 1478, and a T to an A at nucleotide 1273. Similarly, the adenovirus vector AV-GM-CSF may have various deletions within the E1 and E3 regions of its viral genome. Of course, other or additional deletions in the same or other regions of the virus may be possible while retaining relative transfection efficiency.

A variety of antigens and cytokines can be used in the GVAX® vaccine. For example cytokines and antigens of other mammals with substantial homology to the human forms of the cytokines or antigens, are useful in GVAX® vaccine treatment when demonstrated to exhibit similar activity on the immune system. Thus, the GVAX® vaccine method can include treatment with antigens and cytokines, or combinations thereof, combined with other systemic therapy such as chemotherapy, radiation treatments and other biological response modifiers.

The vectors of the GVAX® vaccine which encode the cytokine are used to transduce a tumor cell which is of the type harbored by the patient to be treated with the GVAX® vaccine. The tumor cell may be autologous, i.e., taken directly from the patient or a direct descendent thereof, or may be allogeneic, i.e., from a cell line of the same type as the tumor harbored by the patient.

To produce autologous vaccine cells for each patient, cancer cells needed to be carefully collected under sterile conditions, to be enzymatically disaggregated (as needed, if tumors are solid), to be propagated temporarily in vitro (if cells have been transduced with retrovirus), and then to be transduced with the cytokine-encoding vector to allow high-level paracrine GM-CSF secretion (Wallack et al. (1995) Cancer 75:34-42). If the tumor is solid, at least two grams of surgically harvested tumor cells is typically collected. Thus, autologous GVAX® vaccine treatment for various cancers may depend on the availability of primary tumor tissue with which to make the vaccine.

Unfortunately, for many men suffering with advanced prostate cancer, the autologous tumor vaccine approach is not technically feasible. For these men, and other patients suffering from other cancers, the allogeneic GVAX® vaccine route is of greater benefit, as cancer cell lines are in unlimited supply. Allogeneic cancer cell vaccines contain a substantial fraction of the universe of relevant antigens targetable by the immune system to permit selective cancer cell destruction. As a result, such vaccine preparations may be superior to unspecific antigen vaccines currently in development (such as PSA- or PSMA-based vaccines) because the ideal tumor-associated antigens to target for eliciting therapeutic immune responses are not yet known. In addition, to provide a high chance for antitumor efficacy, the ultimate cancer immunotherapy treatment strategy may need to target several different antigens, just as combination chemotherapy targets several different cellular components, to overcome the striking heterogeneity in gene expression exhibited by nearly all advanced human prostate cancers (Nelson et al. (1996) *Urol. Clin. N. America* 23:685-696).

For allogeneic treatment of prostate cancer, cells derived from an easily propagatable human prostate cancer cell line such as, but not limited to, LNCaP (Peehl in *Atlas of Human Tumor Cell Lines*, pp. 387-407. Acad. Press, Inc., 1994) or PC (Amico et al. (1991) *Clin. Nucl. Med.* 16:643-648; Gerber et al. (1991) *Urol.* 37:418-422), serve as useful sources of prostate cancer antigens for allogeneic prostate cancer vaccine construction. These prostate cancer cell lines were chosen for GM-CSF gene transduction, as between them, they express many of the known tumor antigen expressed by metastatic human prostate cancer cells in patients. Thus, these two cells lines were admixed as one embodiment of an allogeneic prostate GVAX® vaccine.

In another GVAX® vaccine-type approach, a non-cancerous cell expressing an immune system potentiator and/or enhancer, such as a cytokine, is administered to the patient along with the proliferation-incompetent tumor cells as a vaccine. In this "bystander approach" the non-cancerous cells may be modified, for example, by genetic engineering, to express the cytokine using any of the methods described above for genetically modifying the tumor cells (see, e.g., Borrello et al. (Aug. 10, 1999) *Hum. Gene Ther.* 10:1983-1991).

After a patient has gone through GVAX® vaccine treatment, sera are obtained and screened for their ability to recognize cancer-associated or tissue-specific antigens not recognized before treatment. Screening can be accomplished by any known immunological means which utilize the antibodies and other discriminating components of the patient's serum. For example, the tumor-associated antigens can be identified by Western blot analysis, ELISA, radioimmunoassay, or by any number of T cell assays. For example, if an array of proteins from a biological sample is separated via SDS-polyacrylamide gel electrophoresis, a particular tumor-associated antigen may be located in the gel, for example, by Western blotting and the gel slice excised. A variety of other well-known identification methods can be used, such as, for example, staining of side stripes from the edge of the gel or light staining of the gel, itself with, for example, Coomasie blue, sodium acetate, or copper chloride, and locating the band by radioactive labelling with, for example, $^{125}I$, $^{35}S$, $^{32}P$, followed by use of an autoradiogram as a template to excise the band of interest (see, e.g., Harlow and Lane (eds.) *Antibodies, A Laboratory Manual*, Cold Spring Harbor Laboratories, 1988, pp. 61-67).

In one study, carcinoma-related antigens were identified as follows. To prepare autologous prostate GVAX® vaccine, prostate tumors were removed from eight patients to generate primary prostate cancer cell lines. Human GM-CSF-containing retroviral vectors were transduced into these primary cell lines to generate cells secreting GM-CSF. Patients were administered a vaccine in the form of these GM-CSF expressing autologous primary prostate cancer cells every two weeks by intradermal injection. Patients 1, 2, and 3 received $1 \times 10$ cells for six administrations; patient 4 received $1 \times 10^7$ cells for five administrations; patient 5 and 7 received $5 \times 10^7$ cells for six administrations; patient 7 received $1 \times 10^7$ cells for three administrations; and patient 8 received $5 \times 10^7$ cells for three administrations. Sera used for the following studies were prepared from blood taken two hours before vaccination (as pre-vaccination) and two weeks after final vaccination (as post-vaccination).

Identification of the specific antigens recognized by the antibodies in the sera of the patients in autologous prostate GVAX® vaccine trials after final vaccination was made by Western blot analysis of the LNCaP prostate cancer cell line. 25 µg of LNCaP lysate was run on the 4-20% gradient SDS polyacrylamide gels, followed by transference to a nitrocellulose membrane. A dilution in the range of 1:1000 to 1:3000 of patients' sera in PBS containing 0.05% Tween 20 was used for the primary antibody in the Western blot analysis. A dilution of 1:3000 of peroxidase-conjugated-polyclonal goat anti-human IgG+M+A was used for the secondary antibody. The results were developed by chemifluorescence ECL kit.

Figure 2:
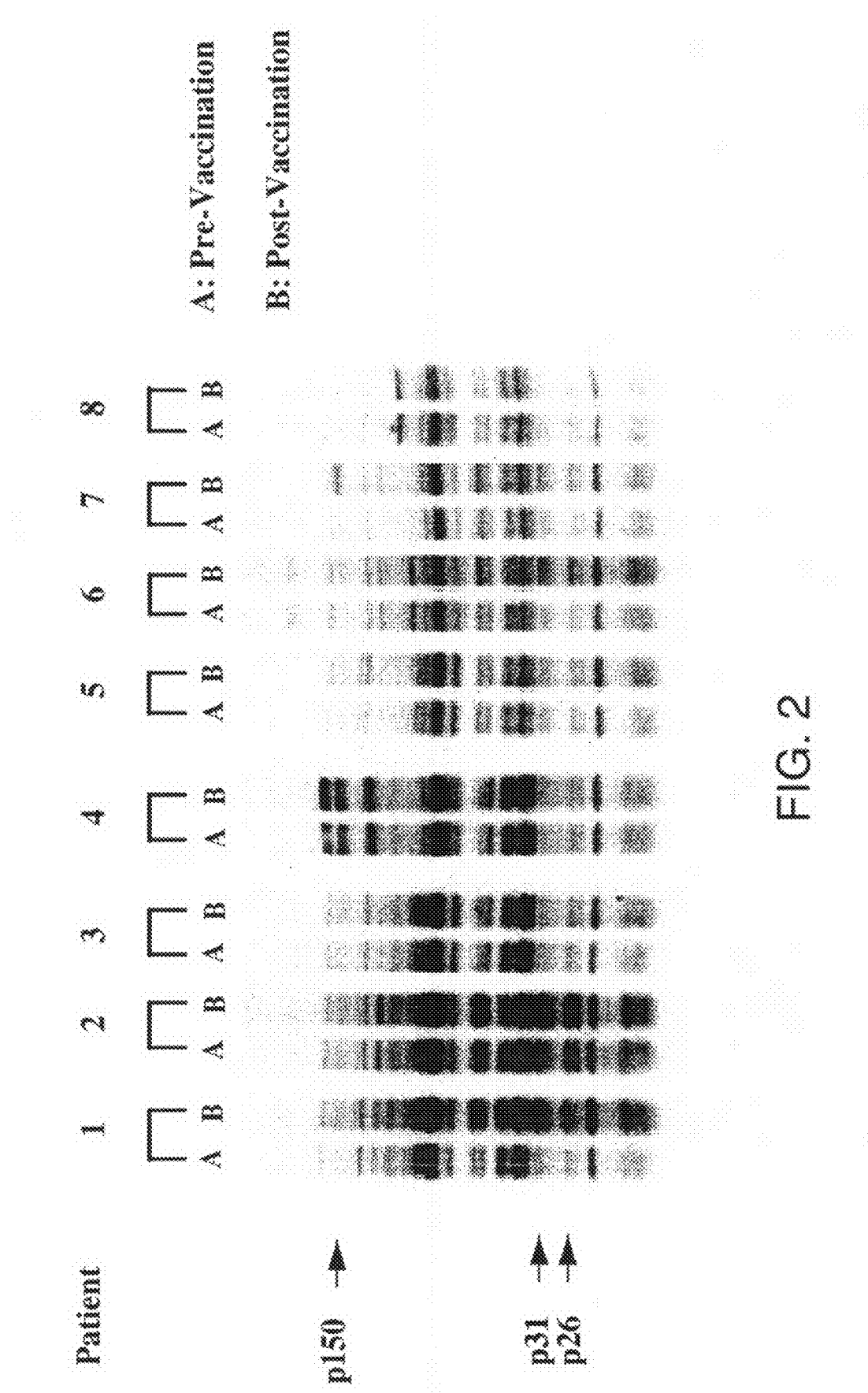
FIG. 2 is a representation of a Western blot in which three antigens (p150, p31, and p26) on LNCaP cells were identified by the sera of 8 patients untreated (A, pre-vaccination) and treated (B, post-vaccination) with autologous prostate GVAX® vaccine.

Three specific antigens from LNCaP cells were novelly identified by comparing the sera derived from pre- and post-vaccination. Sera derived from patients 1 and 6 recognized antigens having an apparent molecular weight of about 26 kD and 31 kD (p26 and p31, respectively), and sera derived from patient 7 recognize a 150 kD protein (p150) and a 26 kD protein (p26) (FIG. 2). The same results were obtained when the lysates derived from two other prostate cancer cell lines (PC-3 and DU-145) were used in western blot analysis.

The molecular weights of the p31 and 26 antigens are very close to the 32 kD molecular weight of PSA. PSA is used as a surrogate marker for the onset and progression of prostate tumor growth. To determine whether the p26 and p31 antigens are related to PSA and whether PSA is being expressed, sera from the autologous GVAX® vaccine-treated patients were examined. 3 µg of purified PSA was run on a 4-20% gradient SDS-polyacrylamide gel followed by Western blotting. Comparing pre- and post-vaccinated sera, no specific antibody response from eight patients in the autologous GVAX® vaccine trial was detected. This result indicates that p26 and p31 are unrelated to PSA.

Figure 3:
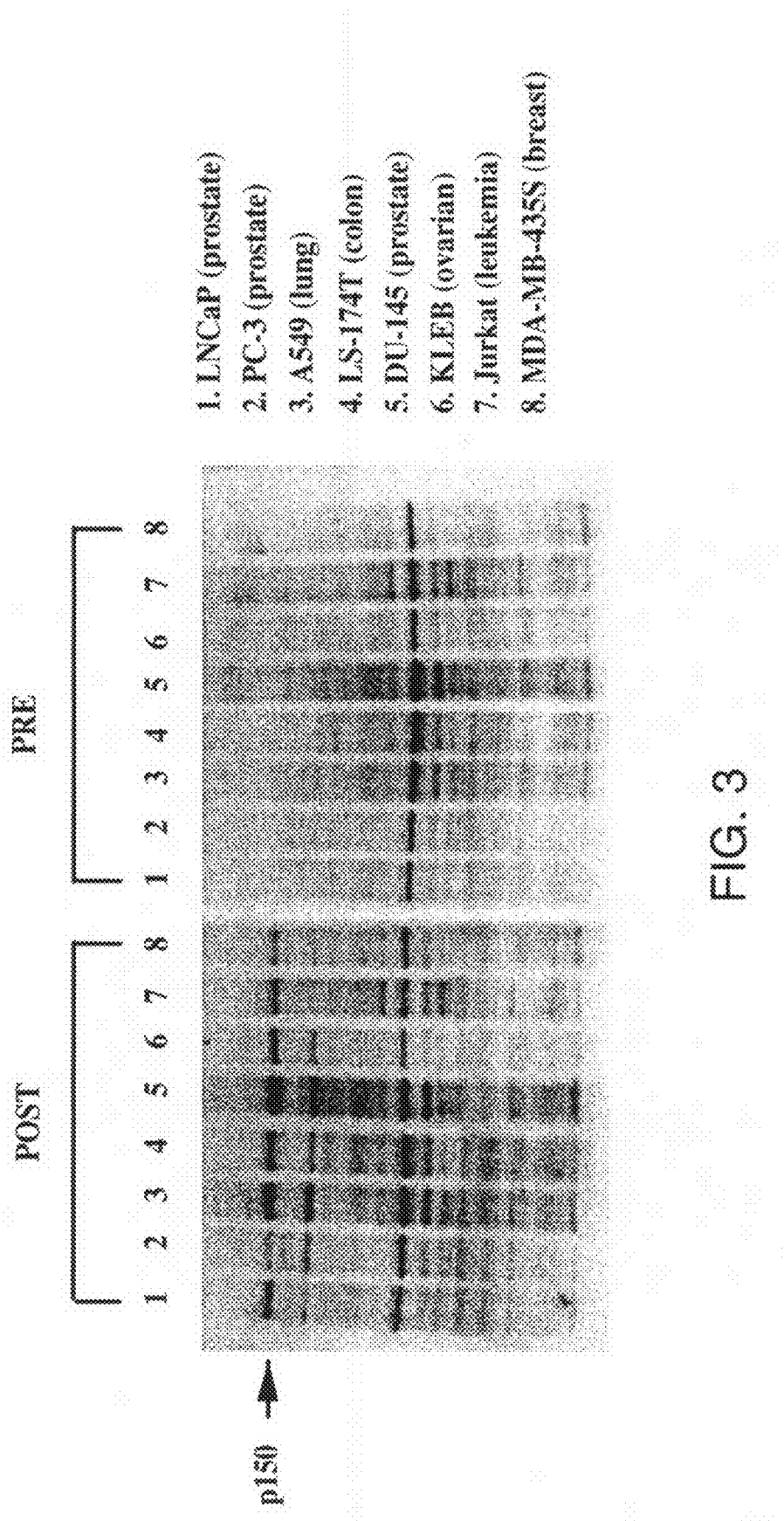
FIG. 3 is a representation of a Western blot in which the p150 antigen was identified by applying pre- and post-treatment sera of an autologous GVAX® vaccine-treated patient to the protein arrays from the following cell lines: (1) LNCaP (prostate carcinoma); (2) PC-3 (prostate carcinoma); (3) A549 (lung carcinoma); (4) LS-174T (colon carcinoma); (5) DU-145 (prostate carcinoma); (6) KLEB (ovarian cancer); (7) Jurkat (leukemia); and (8) MDA-MB-435s (breast carcinoma)

The tissue/cell specific expression of the p150 antigen was characterized by examining its expression in the following different types of cancer cells: LNCaP (prostate carcinoma); PC-3 (prostate carcinoma); A549 (lung carcinoma); LS-1747 (colon carcinoma); DU-145 (prostate carcinoma); KLEB (ovarian carcinoma); Jurkat (leukemia); and MDA-MB-345S (breast carcinoma). By comparing the results obtained by Western blot analysis when pre- and post-vaccinated sera from patient 7 was used, it was determined that p150 is expressed on all of the carcinoma cells lines tested (FIG. 3). This indicates that the novel antigen, p150, is not a prostate tumor-specific antigen, but is rather a "pan" tumor-associated antigen.

Figure 4:
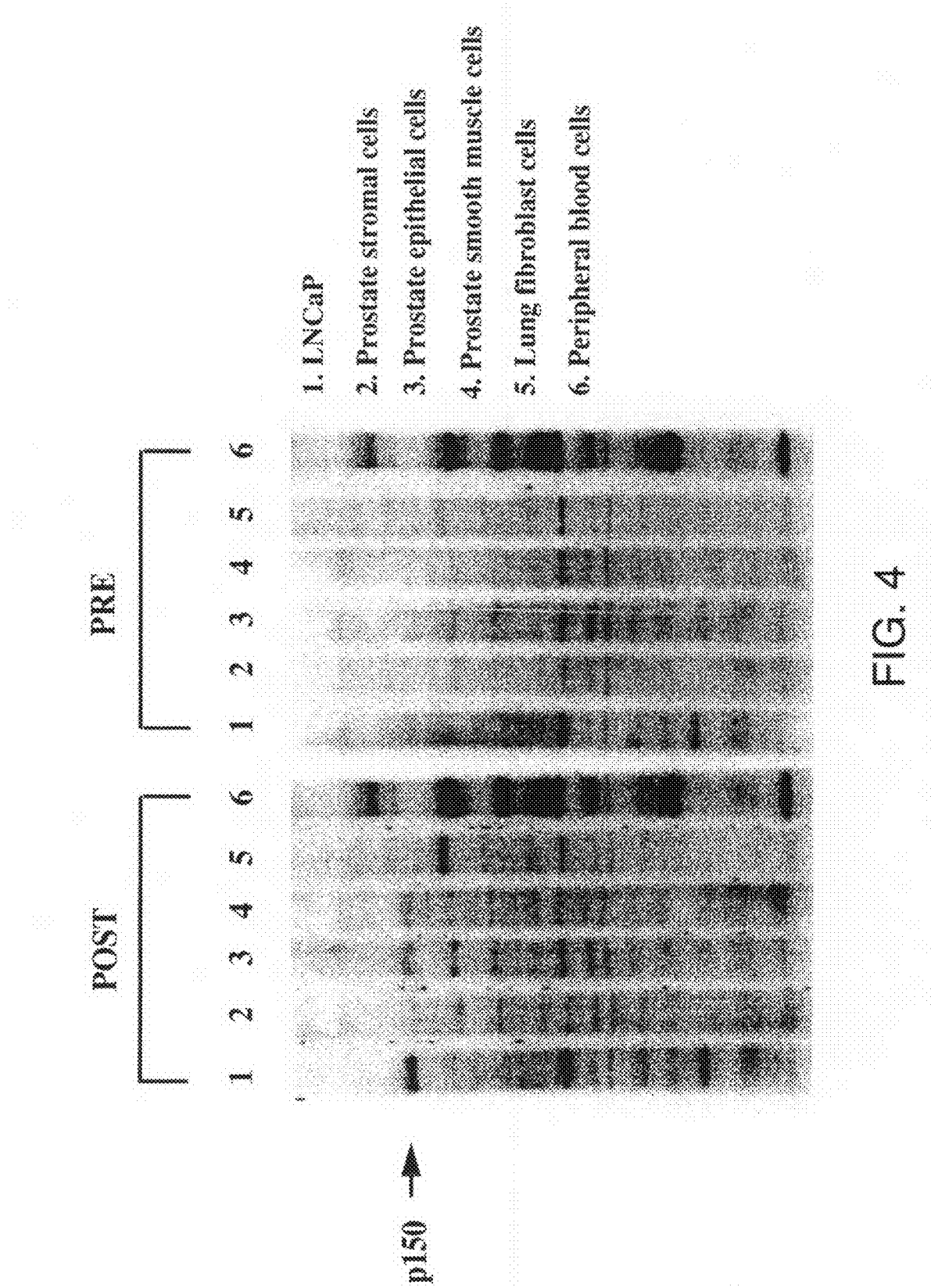
FIG. 4 is a representation of a Western blot in which the expression of the p150 antigen was examined by applying pre- and post-treatment sera to the following cells: (1) LNCaP prostate cancer cell line; (2) normal prostate stromal cells; (3) normal prostate epithelial cells; (4) normal prostate smooth muscle cells; (5) normal lung fibroblast cells; and (6) normal peripheral blood cells.

To determine whether the p150 antigen is a tumor-specific antigen, its expression in normal primary cell lines was examined. Four normal primary cell lines were tested: prostate stromal cells; prostate epithelial cells; prostate smooth muscle cells; and lung fibroblast cells. Freshly isolated peripheral blood cells were also tested. By Western blot analysis and comparing the pre- and post-vaccinated sera derived from patient 7, it was determined that p150 is expressed on prostate epithelial and smooth muscle cells but not prostate stromal cells, lung fibroblast cells, nor peripheral blood cells (FIG. 4). Because p150 is expressed on normal prostate tissues, it may be a tumor-associated antigen that is over-expressed in tumors. These findings also indicate that the GVAX® vaccine can break self-tolerance and enable the immune system to recognize the antigens shared between benign and malignant cells.

Novel antigens were also identified by the sera of patients treated with an allogeneic GVAX® vaccine. In the allogeneic prostate GVAX® vaccine trial, 21 patients were vaccinated with both $1.2 \times 10^7$ GM-CSF-expressing LNCaP (LNCaP/GM) cells and GM-CSF expressing (PC-3/GM) cells weekly for eight weeks. Sera were prepared from blood taken two hours before GVAX® vaccine administration (as "pre-vaccination") and two weeks after final GVAX® vaccine administration (as "post-vaccination").

Figure 5:
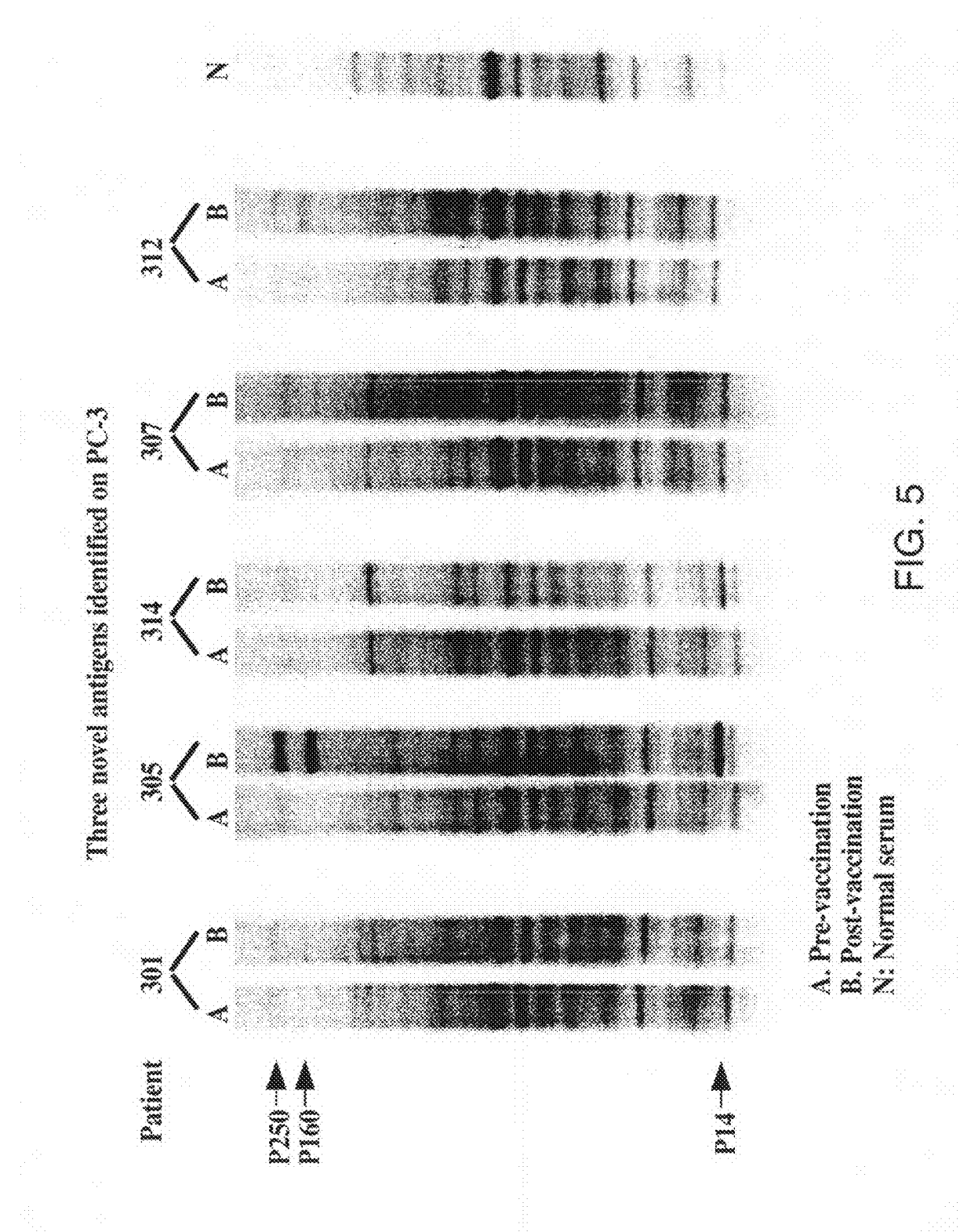
FIG. 5 is a representation of a Western blot in which three antigens (p250, p160, and p14) were identified on PC-3/GM prostate cancer cells by the sera of patients 301, 305, 314, 307, and 312 untreated (A, pre-vaccination) and treated (B, post-vaccination) with allogeneic prostate GVAX® vaccine.

The sera derived from several allogeneic GVAX® vaccine-treated patients were selected for further study. Some of this data is shown in FIG. 5 and is summarized in Table I, below:

TABLE I

| Patient | PC3 Antigen | LNCaP Antigen |
|---|---|---|
| 301 | p14, p18, p27 | |
| 302 | | |
| 303 | | |
| 304 | | |
| 305 | p14, p160, p250, p300 | |
| 306 | p12, p32, p45, p80, p105 | |
| 307 | p32, p43 | |
| 308 | p18 | p40, p55, p68 |
| 309 | p19, p27 | p19 |
| 310 | p250, p300 | |
| 311 | | |
| 312 | | p42, p112 |
| 313 | p70 | |
| 314 | p14, p60, p130 | |
| 315 | p14, p23, p27 | |
| 316 | p250, p300 | |
| 317 | | |
| 318 | | |
| 319 | p29, p43, p60 | |

TABLE I-continued

| Patient | PC3 Antigen | LNCaP Antigen |
|---|---|---|
| 320 | | p150 |
| 321 | p250, p300 | |

Humoral immune responses against LNCAP and PC3 cells were observed in the majority of allogeneic GVAX® vaccine prostate cancer patients. The induction of such anti-PC3 and anti-LNCaP antibody responses, and the observed decrease in PSA velocity in 15 of 21 allogeneic GVAX® vaccine-treated prostate cancer patients, suggest that this humoral immune response may be involved in the initiation of an immune response to eradicate prostate tumor growth in allogeneic GVAX® vaccine-treated patients.

It was next determined whether sera from post-allogeneic GVAX® vaccine treated patients recognize PSA. 3 µg of PSA was analyzed by 4-20% gradient SDS-PAGE followed by Western analysis using the sera from patients 301, 305, 314, 307, and 312. The results show that PSA is not recognized by these sera, indicating PSA cannot be responsible for eliciting the corresponding immune response to eradicate tumor growth.

To further characterize these novel antigens, tissue/cell-specific expression was examined by Western blot analysis using the pre- and post-vaccinated sera derived from patient 305. The following panel of carcinoma cell lines were examined: LNCaP (prostate); PC-3 (prostate); A549 (lung); LS-174T (colon); MCF7 (breast,); DU-145 (prostate); KLEB (ovarian); Jurkat (leukemia); and MDA-MB-435S (breast). The results shown in FIG. 6 demonstrate that p14 is expressed by PC-3 prostate cancer cells. The expression of p14 was also examined in the following primary normal cell lines: prostate stromal cells; prostate epithelial cells; and prostate smooth muscle cells. FIG. 7 shows that p14 is expressed on PC-3 but not any of the primary normal prostate cell lines tested. Taken together, these results strongly indicate that p14 is a prostate tumor-specific antigen.

Figure 6:
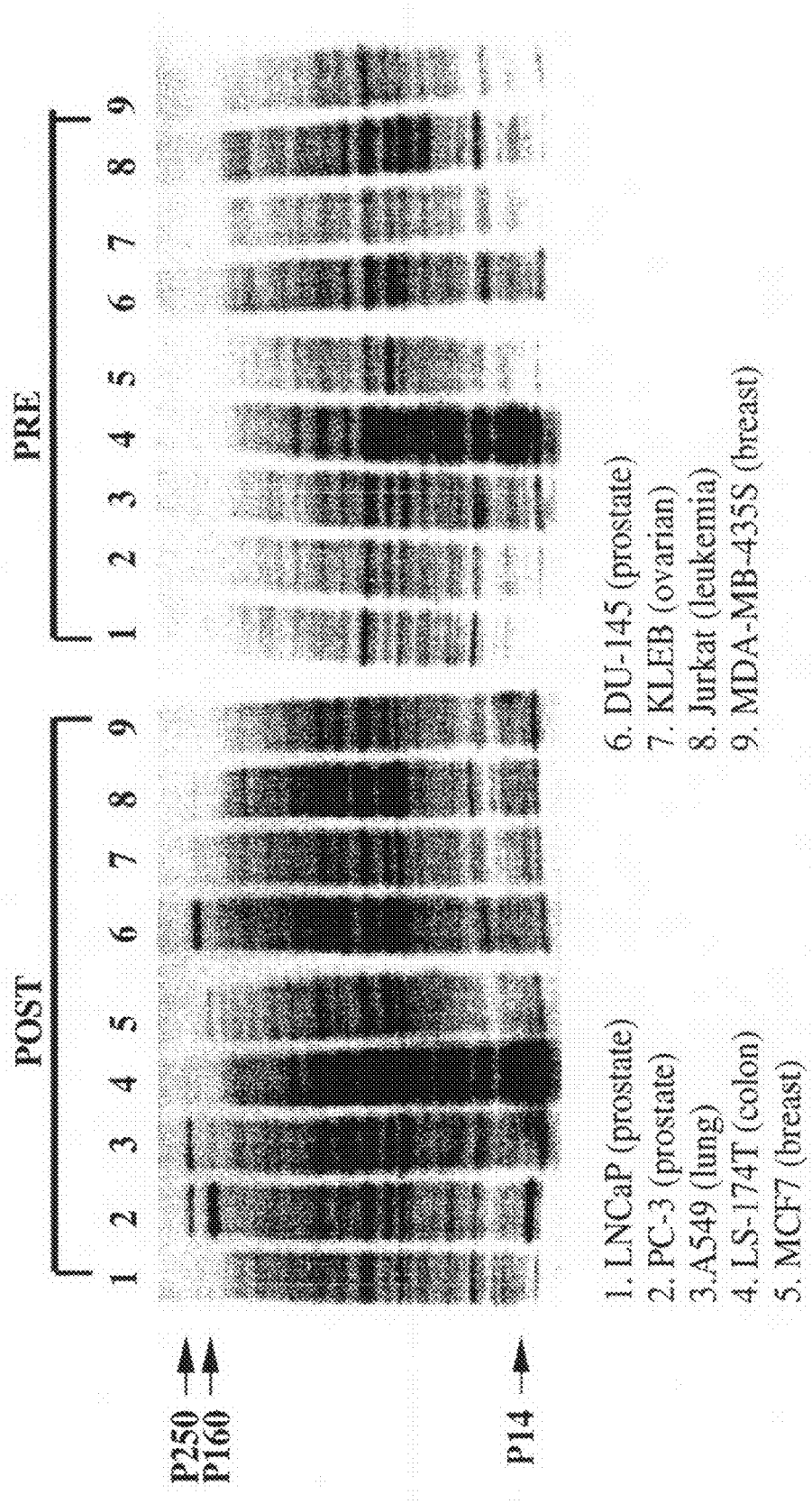
FIG. 6 is a representation of a Western blot in which the p250, p160, and p14 antigens were examined by contact with sera of an-allogeneic GVAX® vaccine-treated patient in the following cell lines: (1) LNCaP (prostate carcinoma); (2) PC-3 (prostate carcinoma); (3) A549 (lung carcinoma); (4)

The tissue/cell-specific expression of the p250 and p160 antigens was also characterized on the same panels of carcinoma cell lines and normal primary prostate cell lines as were used for p14. p160 is expressed on PC-3 cancer and normal prostate epithelial cells, weakly on A549 (lung carcinoma) and MCF7 (breast carcinoma), but not on other types of carcinoma tested, nor on prostate stromal or smooth muscle cells (FIGS. 6 and 7). These results indicate that p160, although not being tumor-specific, is a prostate-specific antigen.

From the same experiments, p250 is found to be expressed on prostate cancer cell lines, PC-3 and DU-145, and A549 lung carcinoma (FIG. 6). P250 is also expressed on normal prostate epithelial cells but not on stromal or smooth muscle cells (FIG. 7). These results strongly indicate that p250, like p160, is a prostate-specific antigen. The fact that there is antibody response to normal prostate-specific antigens, such as p250 and p160, indicates that the allogeneic GVAX® vaccines can break tolerance and cause the immune system to mount a response against such tumors by recognizing prostate-specific antigens.

The identification of such tumor-associated antigens after GVAX® vaccine treatment allows for a rapid assessment of immunologically relevant genes in the tumor. Identification of the tumor-associated antigens encoded by these genes is useful in determining the constituency of protein sequences recognized by the immune system as foreign or as self. Recognition of these sequences may lead to new methods of diagnosis and therapy.

Previous assessments of immunologically relevant antigens did not use tumor immunization as a method for inducing anti-tumor responses. In addition, the adjuvant effects of the GVAX® vaccine could be providing a significant enhancement to tumor immunogenicity, explaining why previous human treatments with autologous or allogeneic tumors did not result in similar findings.

Tumor-associated antigens identified according to the method of the invention described above may then be isolated, further characterized, and cloned. For example, the antigens identified by Western blot analysis may be located in the corresponding SDS-polyacrylamide gel, extracted, and their amino acid sequences determined by methods well known in the art. From these sequences can be derived corresponding oligonucleotides useful in screening various libraries., and then cloning the cDNAs of these antigens.

cDNAs encoding the tumor-associated antigens according to the invention can be cloned by any means known in the art. For example, cloning of the antigen cDNAs can be accomplished by (1) screening cDNA libraries using oligonucleotide probes complementary to the mRNA for these antigens; (2) screening the chips containing EST-tagged genomic libraries using oligonucleotide of identified antigens; and/or (3) screening cDNA expression libraries using sera from the GVAX® vaccine-treated patients. The cDNA library is generated in any known vector systems, including, but not limited to, phage, plasmid, or cosmid, depending on the size of the cDNA encoding a particular antigen. To construct the cDNA library, cDNA is generated from mRNA isolated from the cancer cell lines expressing a particular novel tumor. oligonucleotides specific for the antigen are used to screen the cDNA library to isolate the antigen-specific cDNA by different stringency of hybridization. The cDNA encoding the antigen is then expressed in a cell line which does not normally express this protein. western blot analysis of the transfected cell line using the sera of GVAX® vaccine-treated patients is performed to confirm that the protein encoded by the isolated cDNA is the antigen identified by the sera.

The oligonucleotide probes for the tumor-associated antigens of the invention are also used to screen the chips containing the genomic library of which open-reading fragments were tagged by known oligonucleotide sequences, such as EST tags. The sequence of the antigen-specific cDNAs can be obtained from the well of the chip hybridized at high stringency with oligonucleotides of the antigen. The results obtained from this method enables a search of a cDNA or genomic data base (e.g., at GenBank or the NIH) to identify related cloned proteins. cDNA encoding a novel tumor-associated antigen can be also cloned from an expression library using the GVAX® vaccine sera. cDNA is generated from the mRNA of the cell line expressing the novel tumor antigen(s) of interest and subsequently used to construct expression vectors. These expression vectors contain a promoter for expressing cDNA encoding the antigens in either a prokaryotic or eucaryotic system. The expression library is then transduced or transfected into a host, e.g., a bacterial host cell, using a phage. The duplicates of bacteria/phage colonies are generated on filter membranes. Colonies so formed are lysed and then subjected to Western blotting where positive clones are identified by sera from GVAX® vaccine vaccinated patients. The cDNA of the positive bacteria/phage clones is then isolated and sequenced. This cDNA is then expressed in cell lines and its expression examined by Western blotting using the same patient's sera to confirm that the protein encoded by isolated cDNA corresponds to the previously identified tumor antigen.

The cloned cDNAs or the tumor-associated antigens, themselves, are useful for a number of therapeutic and diagnostic applications, including, but not limited to, the preparation of antibodies which recognize and are reactive with a tumor-associated antigen of the invention, nucleic acid-, vector, protein-, or cell-based tumor-associated vaccines, treatment and/or prevention of various cancers, selection of tumor cell lines for use in an allogeneic GVAX® vaccine, selection of patients for GVAX® cancer vaccine therapy, and development of immune response tests to optimize and guide the development of vaccine therapy.

In a method of screening for the presence of a tumor-associated antigen in a biological specimen, an antibody is prepared to the antigen identified according to the identification method of the invention and then isolated. The biological specimen is contacted with the antibody, and an antigen-antibody reaction detected when the tumor-associated antigen is present in the biological specimen. Of course, standards are analyzed with the antibody as well to determine non-specific background binding and for quantitation of the tumor-associated antigen in the specimen using methods well known in the art.

At least one isolated, tumor-associated antigen of the invention, or an immunogenic fragment or derivative thereof, is also a component of a protein-based vaccine as provided by the invention. Immunogenic fragments of the tumor-associated antigen can be identified, for example, by determining what portion of the protein is still recognized by the GVAX® vaccine-treated patient's sera which originally recognized the entire antigen. The antigen or portion thereof can be formulated with physiologically acceptable carrier and adjuvants to make a classic protein vaccine. One useful carrier is physiological saline. Non-limiting examples of useful adjuvants include oil in water, mycobacterium, and bacterial adjuvants. The vaccine can further contain an immune system potentiator and/or enhancer at a nontoxic concentration, or alternatively, a cell expressing such a potentiator and/or enhancer. A variety of immune system potentiators and/or enhancers will find use in the present invention. Non-limiting examples of such potentiators and/or enhancers include GM-CSF, IL-1, IL-3, IL-4, IL-6, IL-7,IL-10, CD2, IL-12, IL-15, IL-18, TGF-β, B7, MIP-1α, MIP-1β, MIP-2, M-CSF, G-CSF, and/or ICAM. In addition, potentiators and/or enhancers of other mammals with substantial homology to the human forms of the same are useful in the invention when demonstrated to exhibit similar activity on the immune system. Furthermore, the vaccines of the present invention can be combined with other systemic therapy such as chemotherapy, radiation treatments and other biological response modifiers.

Other vaccines are nucleic acid-based vaccines, including a nucleic acid encoding at least one novel tumor-associated antigen, or antigenic fragment thereof, and a nucleic acid encoding at least one protein-based potentiator and/or enhancer, such as GM-CSF. The tumor-associated antigen is not tumorigenic and may be a marker protein. A tumorigenic protein causes a cell to become cancerous, one characteristic of which is its ability to grow uncontrollably. Representative, nonlimitng methods of testing the tumorigenicity of a tumor-associated antigen are the following. Target non-tumor cells plated on a multiwell plate at a density of approximately 50,000-100,000 cells/well. Tumor-associated antigen or vectors encoding the tumor-associated antigen are added to the cells. The cells are similarly treated daily for 7 days. Then, the cells are harvested and approximately 2,000-5,000 live cells are plated in soft agar, for example, as described in Freedman and Shin, Cell 3:355-359 (1974). Two weeks after plating, the number of colonies formed in soft agar are scored by visual examination. If the tumor-associated antigen is tumorigenic, a dose-dependent increase in the number of colonies is observed relative to colonies formed by untreated cells.

Alternatively, BALB/c nude mice (Taconic Labs, Great Barrington, N.Y.) can be injected subcutaneously in the flank area with approximately $2\times10^6$ non-tumor cells treated with a tumor-associated antigen or a nucleic acid or vector encoding the same. Formation of a tumor is indicative of the tumorigenicity of the tumor-associated antigen Preferably, the nucleic acid in the vaccine is RNA or DNA, which may be genomic DNA or cDNA. The nucleic acids encoding the tumor-associated antigen and potentiator and/or enhancer may be carried together or separately on one or more vector, such as viral vector. Useful viral vectors are those described above for use in the GVAX® vaccine methods. Two representative viral vectors are depicted schematically in FIGS. 8A and 8B. Alternatively, non-viral vectors comprising plasmid DNA, either alone or formulated with, e.g., liposomes and protein condensers (e.g., poly-lysine compounds) can also be used. The DNAs or vectors may then be administered using known gene therapeutic methods.

The DNAs or vectors encoding a novel tumor antigen, or fragment thereof, can also be used to genetically engineer a cell to produce and present the tumor antigen. This cell is then used in a cell-based vaccine of the invention. As in the GVAX® vaccine method described above, the cell to be genetically engineered may be an allogeneic or autologous cell. These GVAX®-type vaccines may be optimized using the defined novel cancer antigens. Optimization can be accomplished by using the tumor-associated antigens to select tumor cell lines that have high expression levels and a broad cancer antigen repertoire. In this way, a combination of cell lines can be selected with optimal cancer antigen composition. Since it is possible that more than one cancer antigen will be used to cover all patients who may have varied cancer gene expression in their tumors, and to prevent immunologic escape by in vivo tumor mutation against a single antigen, multiple cancer antigens have been and are being identified. As a corollary, in some embodiments, a cancer vaccine of the invention contains or encodes multiple antigens.

The present invention also provides methods of using the antigens and vaccines of the invention, including treatment of primary and/or metastatic tumors. For example, the novel tumor-associated antigens identified according to the method of the invention can be used to stimulate and expand a patient's tumor-specific T cells ex vivo. These activated T cells can then be returned to the patient to elicit an anti-tumor response. In addition, the present invention includes vaccines useful for preventive purposes, e.g., to protect an individual against development or progression of a tumor. For treatment purposes, the vaccine is administered in a therapeutically effective amount and in a therapeutically effective manner.

As used herein, the term "therapeutically effective amount" means the total amount of each active component of the vaccine or method that is sufficient to show a meaningful subject or patient benefit, i.e., a reduction in tumor growth or in the expression of proteins which cause or characterize the cancer. When applied to an individual active ingredient, administered alone, the term refers to that ingredient alone. When applied to a combination, the term refers to combined amounts of the active ingredients that result in the therapeutic effect, whether administered in combination, serially or simultaneously.

A "therapeutically effective manner" refers to a route, duration, and frequency of administration of the pharmaceutical formulation which ultimately results in meaningful patient benefit, as described above. For example, the vaccine of the invention may be administered intradermally, intramuscularly, or subcutaneously via injection. Alternatively, the vaccines of the invention, such as, but not limited to, a protein-based vaccine, may be administered sublingually, rectally, orally, or enterally in bolus, continuous, intermittent, or continuous, followed by intermittent regimens.

The therapeutically effective amount of vaccine of the present invention will depend upon the nature and severity of the condition being treated, and on the nature of prior treatments which the patent has undergone. Ultimately, the attending physician will decide the amount and type of vaccine with which to treat each individual patient. Initially, the attending physician may administer lower doses of the vaccine and observe the patient's response. Larger doses of the vaccine may be administered until the optimal therapeutic effect is obtained for the patient, and at that point the dosage is not increased further.

The identification of antigens identified by GVAX® vaccine immunized patients' humoral responses is an important step in selection of immunodominant tumor rejection antigens. The validation of an antigen as being clinically important for immunotherapeutic treatment in cancer involves the correlation of tumor-associated, antigen-specific immune responses with clinical anti-tumor responses, followed by a clinical trial using an optimized dose schedule of a vaccine comprised of these tumor-associated antigens that shows a statistically significant clinical effect associated with the immune response against these antigens.

The correlation of antigen immune responses are performed by comparing clinical endpoints with the qualitative and quantitative assessment of the tumor-specific immune response. This correlation, from a statistical standpoint, can be evaluated on either a proportional or continuous (uninterrupted) association. For example, in one case, the clinical endpoint of a 50% decrease in PSA from baseline three months after the first vaccination is considered to be a defined positive clinical result. The proportion of patients that meet the criteria for this endpoint and also have an immune response against the antigen on Western blot is compared to the patients that do not meet this criteria and have expression of the same immune response to the antigen on the Western blot. If there is a significant increase in patients that meet the positive clinical criteria and have the antibody to the antigen compared to patients with negative clinical response and no antibody, then a correlation is suggested.

The slope of the PSA velocity is an example of a quantitative continuous variable. For this assessment the slope of the PSA velocity at a defined interval prior to receiving treatment is compared to the slope of the PSA velocity at a defined interval after treatment. PSA values taken every two weeks for the pre- and post-treatment periods provide the raw data for this calculation. The percent shift in slope can be calculated for this analysis. Progressive prostate cancer is defined as a positive percent change in slope. A positive therapeutic result is defined as any negative percent change in slope. The mean or median percent change in slope of patients that have an immune response to specific cancer antigens can be analyzed and evaluated for significance. The advantage of this analysis is that it incorporates all the clinical data and that it is quantitative.

These types of analyses are used to evaluate the presence of immune response to antigens for all relevant clinical endpoints including PSA, PSA velocity, survival, disease free survival, time to progressive disease, time to initiation of alternative therapy, quality of life, bone pain, etc. The type of immune response to antigens that can be correlated is not limited to presence of antigens, but includes quantitative antigen-specific antibody assays such as ELISA or RIA and antigen-specific cellular assays such as CD4 proliferation assays or CD8 CTL lysis assays.

Other uses of the novel tumor-associated antigens of the invention include diagnostic methods of detecting tumor-associated antigens in a biological sample taken from a subject. These detection methods, in turn, are useful for selection of patients for vaccine therapy and to guide optimal therapy. Antibody-based assays, polymerase chain reaction, and nucleic acid hybridization assays specific for the tumor-associated antigens are non-limiting examples of useful detection methods. Biological samples from the patients are analyzed for the presence of these tumor-associated antigens, and the appropriate tumor-associated antigen vaccine of the invention is then administered. Repeat analyses for the patients' tumors may be done to evaluate the efficacy of the vaccine and whether or not mutations have altered the array of cancer antigens in the patient. This method works well as a diagnostic and therapeutic efficacy assay with cancer antigens that are tumor-specific.

Methods to detect whether the immune system of a patient has developed an immune response against the tumor-associated antigens are useful to guide therapy. Such methods include, but are not limited to, antibody based assays (ELISA, RIA, Western blot), antigen specific-cellular assays, proliferation assays, cytolytic cell assays, and in vivo delayed-type hypersensitivity testing with recombinant tumor-associated antigen or immunogenic fragments or peptides from the antigen. These assays are useful in phase II dose optimization studies to determine whether the antibody or cellular arm of the immune system has generated a cancer antigen specific-response. The information obtained from these assays and studies is useful for altering the dose or schedule of the cancer antigen vaccine, and for optimizing the treatment with the vaccine for drug approval and for an individual patient's therapy.

The most useful antibodies are those generated by tumor-associated antigens of the invention. However, in some cases, cross-reacting antibodies will be found that have been elicited by a closely related antigen rather than by a tumor-associated antigen of the invention.

The present invention also encompasses preparations of polyclonal and monoclonal human, chimeric, and humanized antibodies directed to the novel tumor-associated antigens, cells, and cell S lines of the invention, including tumor-associated antigen-expressing and tumor associated antigen- and cytokine-expressing autologous and allogeneic tumor and-normal cells. These antibodies can then be used to prepare antibody-containing compositions used in the diagnostic and therapeutic methods of the present invention.

The antibodies are prepared via techniques well known to those having ordinary skill in the art (see, e.g., Harlow and Lane (eds.) *Antibodies, A Laboratory Manual*, Cold Spring Harbor Laboratories, 1988). In particular, monoclonal antibodies produced against immortal tumor cell lines according to the present invention are useful in the detection and therapy of various cancers, such as prostate cancer. The antibody or antigen binding portion thereof binds to malignant cells. Thus, the antibody or antigen binding portion thereof is immunoreactive with at least one tumor rejection antigen or with at least one tumor-associated antigen and epitopes thereof.

Exemplary antibody molecules are intact immunoglobulin molecules, substantially intact immunoglobulin molecules or those portions of an immunoglobulin molecule that contain the antigen binding site, including Fab, $F(ab)^2$, and $F(v)$. Polyclonal or monoclonal antibodies may be produced by methods known in the art. (Kohler and Milstein (1975) *Nature* 256:495-497; and Campbell, in Burdon et al. (eds.) (1985), *Laboratory Techniques in Biochemistry and Molecular Biology*, Vol. 13, Elsevier Science Publishers, Amsterdam). The antibodies or portions thereof may also be produced by genetic engineering including chimeric antibody, single chain antibody (see, e.g., Traunecker et al. (1991) *EMBO J.* 10:3655-3659; and Milenic et al. (1991) *Cancer Res.* (1991) 51:6363-6371), and humanized antibody (see, e.g., U.S. Pat. No. 5,530,101)

The antibody or portion thereof may be used as an immunotherapeutic. The antibody or portion thereof may be administered alone, or in combination with chemotherapeutics or immunosuppressive agents as are known in the art.

The antibody or portion thereof may also be used as an immunotoxin to specifically target and kill malignant primary and metastatic cells. Immunotoxins are characterized by two components and are particularly useful for killing selected cells in vitro or in vivo. One component is a cytotoxic agent which is usually fatal to a cell when attached or absorbed. The second component, known as the delivery vehicle, provides a means for delivering the toxic agent to a particular cell type, such a malignant prostate cells. The two components are commonly bonded together by any of a variety of well-known chemical procedures. For example, when the cytotoxic agent is a protein, the linkage to the antibody may be by way of hetero bifunctional crosslinkers, e.g., SPDP, carbodiimide, glutaraldehyde, and the like. Production of various immunotoxins is well-known in the art (see, e.g., Thorpe et al., *Monoclonal Antibodies in Clinical Medicine*, Academic Press, pp. 168-190 (1982)). The components may also be linked genetically as described in Chaudhary et al. (*Nature* (1989) 339: 394).

A variety of cytotoxic agents are suitable for use in immunotoxins. Cytotoxic agents include, but are not limited to, radionuclides, such as Iodine$^{131}$ or other isotopes of iodine. Yttrium$^{90}$, Thenium$^{188}$, and Bismuth$^{212}$ or other alpha emitters; a number of chemotherapeutic drugs, such as vindesine, methotrexate, andriamycin, taxol, and ciplatinum; and cytotoxic proteins such as ribosomal inhibiting proteins like *Pseudomonas* exotoxin A, ricin, diphtheria toxin, ricin A chain and the like (see Olsnes et al. (1982) *Pharmacol. Ther.* 25:355-381; and "Monoclonal Antibodies for Cancer Detection and Therapy", eds. Baldwin and Byers, pp. 159-179, and 224-266, Academic Press, 1985).

For diagnostic purposes, the antibody may be either labeled or unlabeled. Unlabeled antibody may be used in combination with other labeled antibodies. A wide variety of labels may be employed, such as radionuclides, fluors, enzymes, enzyme substrates, enzyme cofactors, enzyme inhibitors, ligands and the like. Numerous types of immunoassays are available and are well-known to those skilled in the art.

Antibodies of the invention may also be components of kits for screening for the presence of a tumor-associated antigen in a biological sample. The kits of the invention comprise unlabelled first antibodies directed to a tumor associated antigen, the tumor-associated antigen being reactive with serum from a subject treated with a GVAX®-type vaccine, but not being reactive with serum from the subject before treatment with the vaccine. The kits also comprise a solid support for adhering the first antibodies thereto, This support may be plastic. Preferably the solid support is a dish, slide, bead, or other structure useful for the adherence of antibody. The kit also includes labelled second antibodies. The second antibodies may be directed to the first antibodies. For example, if the first antibodies are human, humanized, or are chimeric antibodies containing portions of a human antibody, the second antibody can be an anti-human antibody. Alternatively, if the first antibodies are from a non-human mammal, the second antibodies are directed specifically to those non-human, mammalian antibodies. The second antibodies may be monoclonal antibodies directed to a different epitope on the tumor-associated antigen that the first antibodies which are also monoclonal antibodies.

The first antibodies adhered to the biological support are contacted with a biological sample from a subject to be screened for cancer. Such a sample includes any sample taken from a subject or a cell line in a form that enables protein antigens therein to recognize and react with the antibodies on the support. Useful biological samples include, but are not limited to, blood, serum, a tissue biopsy, spinal fluid, saliva, lacrimal secretions, semen, vaginal secretions, feces, urine, ascites fluid, or a tumor cell line. The biological sample may be processed to make available for binding the protein antigens therein. For example, a tissue or cell sample may be processed by homogenization. If the biological sample contains a tumor-associated antigen or antigen which cross-reacts with the first antibodies directed to a tumor-associated antigen, this antigen will react with the antibodies on the support. The addition of the second labelled antibodies directed to the first antibodies or to a different epitope of the tumor associated antigen enables the identification of the tumor-associated antigen in the biological sample.

The following examples serve to more fully describe the manner of making and using the above-described invention, as well as to set forth the best modes contemplated for carrying out various aspects of the invention. It is understood that these examples in no way serve to limit the true scope of this invention, but rather are presented for illustrative purposes.

EXAMPLES

1. Clinical Trials Using the GVAX® Vaccine

A. Generation of Recombinant Viral Vectors Encoding cytokines for Preparation of GVAX® Vaccines The following viral vectors encoding a cytokine were constructed for introduction into tumor cell lines or into primary tumor cells obtained from resected human tumors.

(1) Retroviral Vectors

Construction of retroviral vectors employs standard ligation and restriction techniques which are well understood in the art. A variety of retroviral vectors containing a gene or genes encoding a cytokine of interest were used. The MFG vector is described in U.S. Ser. No. 07/607,252 entitled "Genetic Modification of Endothelial Cells", filed Oct. 31, 1990, U.S. Ser. No. 07/786,015; "Retroviral Vectors useful in Gene Therapy", filed Oct. 31, 1991, and PCT/US91/08121, filed Oct. 31, 1991, the teachings of which are incorporated herein by reference. They are also described below with particular reference to the incorporation and expression of genes encoding cytokines. Furthermore, several MFG vectors have been deposited with the ATCC: the unmodified MFG vector was deposited as ATCC accession no. 68754; an MFG vector with a factor VIII insertion was deposited as ATCC accession no. 68726; and the MFG vector with a tPA insertion was deposited as ATCC accession no. 68727, These deposits were made under the provisions of the Budapest Treaty on the International Recognition of the Deposit of Microorganisms for the purposes of patent procedure and the Regulations thereunder.

The MFG vector is similar to the pEm vector, described below and depicted in FIG. 1C, but contains 1038 base pairs of the gag sequence for MoMuLV, to increase the encapsidation of recombinant genomes in the packaging cells lines, and 350 base pairs derived from MOV-9 which contains the splice acceptor sequence. An 18 base pair oligonucleotide containing Nco I and BamHI sites directly follows the MOV-9 sequence and allows for the convenient insertion of genes with compatible sites. The coding region of the gene was introduced into the backbone of the MFG vector at the Nco I site and BamHI site. The ATG initiator methionine codon was subcloned in frame into the Nco I site and little, if any, sequence beyond the stop codon was included, in order to avoid destabilizing the product and introducing cryptic sites. As a result, the ATG of the insert was present in the vector at the site at which the wild-type virus ATG occurs. Thus the splice was essentially the same as occurs in Moloney Murine Leukemia virus and the virus worked very well. The MoMuLV LTR controls transcription and the resulting mRNA contains the authentic 5' untranslated region of the native gag transcript followed directly by the open reading frame of the inserted gene. In this vector, Moloney murine leukemia virus (Mo-MuLV) long terminal repeat sequences were used to generate both a full length viral RNA (for encapsidation into virus particles), and a subgenomic mRNA (analogous to the Mo-MuLV env mRNA) which is responsible for the expression of inserted sequences. The vector retained both sequences in the viral gag region shown to improve the encapsidation of viral RNA and the normal 5' and 3' splice sites necessary for the generation of the env mRNA. All oligonucleotide junctions were sequenced using the dideoxy termination method and T7 DNA polymerase (Sequenase 2). The structure of MFG is represented in FIG. 1A. As can be seen, the virus is marker-free in that it does not comprise a dominant selectable marker (although one may optionally be inserted), and, given the high levels of transduction efficiency and expression inherent in the structure of the vector, transduction with MFG derivatives generally does not involve or require a lengthy selection step.

MFG vectors containing genes for the following proteins were constructed: murine IL-2, GM-CSF, IL-4, IL-5, γ-IFN, IL-6, ICAM, CD2, TNF-α, and IL-1-RA (interleukin-1-receptor antagonist). In addition, human sequences encoding TNF-α, GM-CSF and IL-2 were constructed. It is also possible to make MFG vectors containing a gene encoding one or more of the following: VCAM, ELAM, macrophage inflammatory protein, heat shock proteins (e.g., hsp60), M-CSF, G-CSF, IL-1, IL-3, IL-7, IL-10, IL-12, IL-15, TGF-β, B7, MIP-2, MIP-1α and MIP-1β.

Precise cDNA sequences subcloned into MFG were as follows: murine IL-2 base pairs 49-564; murine IL-4 base pairs 56-479; murine IL-5 base pairs 44-462; murine GM-CSF (29) base pairs 70-561; murine ICAM-1 base pairs 30-1657; murine CD2 base pairs 48-1079; murine IL-1 receptor antagonist base pairs 16-563; human TNF-α base pairs 86-788.

(2) Adenoviral Vectors

The adenovirus transducing human GM-CSF (AV-GM-CSF) contains a GM-CSF expression cassette substituted for the E1 genes of adenovirus type 5 with an additional deletion in the viral genome in the E3 region. According to the complete GenBank sequence for Ad5 (Accession no. M73260), the deletions are from 455 to 3327 in the E1 region. Numbering begins with the first base of the left inverted terminal repeat.

Construction of the adenoviral vectors employs standard ligation and restriction techniques which are well understood in the art. The E3 deletion was introduced by overlap recombination between wild type 300 (from H. Ginsberg) (0 to 27330) and dl324 (Thimmappaya et al. (1982) *Cell* 31:543-551) (21561 to the right end). The GM-CSF expression cassette was added to the E1 region by cre/lox mediated recombination between pAdlox MC hGM and E3 deleted adenovirus in CRE8 cells (Hardy et al. (1997) *J. Virol.* 71:1842-1949). pAdlox MD hGM was derived from pAdlox (Hardy et al. (1997) and pMD.G (Naldini et al, (1996) *Science* 272:263-267) and contains the following sequences: 0 to 455 from Ad5, the cytomegalovirus (CMV) immediate early gene promoter/enhancer (nucleotide positions −670 to +72, GenBank accession no. X03922) from pBC12/CMV/IL-2 (Cullen (1986) *Cell* 46:973-982), a small region of human β-globin exon 2 and a shortened second intervening sequence (IVS2) (nucleotide position 62613-62720 plus 63088-63532, GenBank accession no. J00179), exon 3 and the poly adenylation signal from human β-globin (nucleotide positions 63532-64297), the GM-CSF cDNA inserted into exon 3 (position 63530), a second poly adenylation site from SV-40 (position 2681-2534), (GenBank accession no. J02400) and a loxP site followed by bacterial sequences from Bluescript. The GM-CSF cDNA was obtained from a plasmid (DNAX Research Institute of Molecular and Cellular Biology (Palo Alto, Calif.)). The DNA sequence was isolated from cDNA libraries prepared from Concanavalin A-activated human T-cell clones by functional expression in mammalian cells. The isolation and characterization of the cDNA, including the entire sequence of the gene, have been reported in the scientific literature. (Lee et al. (1985) *Proc. Natl. Acad. Sci. (USA)* 82:4360-4364). The identity of the clone was verified by restriction endonuclease digestion upon receipt. The MD expression cassette was modified by PCR to include restriction sites for PmlI, EcoRI and Bgl II for insertion of a transgene downstream of the IVS2. The GM-CSF cDNA was removed using PmlI and BamHI from pMFG-S hGM (Dranoff et al. (1997) *Human Gene Ther.* 7:111-123) and inserted into the PmlI and Bgl II sites in the MD cassette. The region of the pAdlox MD hGM plasmid that was incorporated into the adenovirus (Ad GM virus) was sequenced on both strands. Correct structure of the initial viral construction was confirmed by restriction analysis and ELISA testing for GM-CSF production from infected HeLa cells. The recombinant virus was then subjected to two rounds of plaque purification. Recombinant virus from a plaque was restriction mapped and expanded two passages by growth in 293 cells (certified cells from Microbiological Associates) to produce a research virus stock. The sequence of the GM-CSF gene in the virus was determined by direct sequencing of viral DNA prepared from the research virus stock. Finally, recombinant virus from the research virus stock was tested for mycoplasma and sterility, and when found negative, used to infect cells for the master virus stock.

B. GVAX® Vaccine treatment (1) Autologous Prostate GVAX® Vaccine Trials

The nine patients enrolled were greater than 18 years old with progressive, micrometastatic prostate cancer after surgery as defined by two successive abnormal elevations in PSA levels, without evidence of measurable metastatic disease or prior hormonal therapy, and with at least a baseline PSA of greater than 1.0 ng/ml at the start of treatment. The patients underwent surgery with appropriate concomitant medications. Pathologic diagnosis and staging of disease was completed during surgery.

A portion of the resected tumor was expanded in primary culture, transduced with the MFG viral vector carrying the GM-CSF gene, irradiated to render the cells proliferation-incompetent, and stored in liquid nitrogen until used to prepare the autologous GVAX® vaccine. Approximately 60 days after surgery, the vaccine was available for use at the clinical site. For each vaccination, the GVAX® vaccine was prepared and formulated for injection by thawing, washing, and resuspension of the cells in 0.9% sodium chloride solution or in 0.9% sodium chloride solution containing 2.5% human serum albumin.

Approximately 60 days after surgery, a prevaccination visit was scheduled to obtain baseline values and to initiate the first DTH evaluation of autologous, nontransduced cells. Serum was taken and PSA levels measured by RT-PCR. Two days after the prevaccination visit, each patient was scheduled through three vaccination cycles of 14 days each. If after three vaccinations there was no evidence of cumulative toxicity, and if sufficient vaccine cells remained, the patient was eligible to receive up to three additional vaccinations, for a total of six vaccinations.

The spacing and location of the vaccination sites are presented in Table II below. Each dose was administered to the patient on an outpatient basis, followed by clinical observation in the outpatient's department before discharge.

TABLE II

VACCINATION TECHNIQUE

| Dose Level | Dose Injected | Cells/ml | Injection Volume | Injections |
|---|---|---|---|---|
| 1 | $1 \times 10^7$ | $1 \times 10^7$ | 0.5 cc | 2 |
| 2 | $5 \times 10^7$ | $2.5 \times 10^7$ | 0.5 cc | 5 |

Injections were given intradermally in the patients' limbs following a grid pattern. Each injection is at least 5 cm at needle entry from the nearest neighbor injection. For Dose Level 1, injections were given to three patients in one limb using a different limb in each successive cycle. For Dose Level 2, the injections in six patients were equally divided between two limbs in a given cycle, using two different limbs in each successive cycle. The first vaccination occurred on day 0 and subsequently on days 14, 28, 42, 56 and 70. Evaluation for local and systemic toxicities and induction of anti-tumor immune responses followed. Evidence of autoimmunity was also assessed.

No NCI CTC dose limiting toxicities were observed among eight vaccinated patients who received a total of 41 fully evaluable vaccinations. Biopsies of intradermal sites displayed distinctive inflammatory infiltrate, composed of macrophages, dendritic cells, eosinophils and T-cells similar to those observed in preclinical models of efficacy. 100% of patients displayed DTH reactivity to untransduced, autologous PCA target cells. The median serum PSA before surgery was 28.85 (with a range of 6.7-7.5) and the median PSA level at first vaccination was 0.65 (with a range of 0.1-30.4). By ultrasensitive serum PSA, 6/8 patients progressed after surgery and vaccination: average F/U 24 months. This study demonstrates the feasibility, outpatient safety, and bioactivity of in vivo GM-CSF gene-transduced PCA vaccines for Phase II trials powered to estimate efficacy.

(2) Allogeneic Prostate GVAX® Vaccine Trials

The 30 patients enrolled were greater than 18 years old with progressive, micrometastatic prostate cancer after surgery as defined by two successive abnormal elevations in PSA levels, without evidence of measurable metastatic disease or prior hormonal therapy, and with at least a baseline PSA of greater than 1.0 ng/ml at the start of treatment.

The allogeneic prostate cancer cell line vaccine is composed of two equal cell doses of allogeneic prostate cancer cell lines (LNCaP 1740 and PC-3) genetically modified to secrete 148-639 ng of GM-CSF/$10^6$ cells/24 hours. Alternatively, the vaccine is composed of a mixture of three different irradiated, autologous prostate cancer cell lines (LNCaP, PC-3 and DU 145) genetically modified to secrete 200-300 ng of GM-CSF/$10^6$. Each vial of vaccine is prepared as a direct injectable in glycerol and human serum albumin. The dose of each cell line vaccination is presented in Table III below.

TABLE III

VACCINATION TECHNIQUE

| Cell Line | Dose Injected | Cells/ml | Injection Volume | Injections |
|---|---|---|---|---|
| LNCaP-1740 | $6 \times 10^7$ | $3 \times 10^7$ | $2 \times 1.0$ cc | 2 of $3 \times 10^7$ cells |
| PC-3 | $6 \times 10^7$ | $3 \times 10^7$ | $2 \times 1.0$ cc | 2 of $3 \times 10^7$ cells |

On a given vaccination day, the patient receives a total of $1.2 \times 10^8$ total cells ($6 \times 10^7$ cells per cell line), given in 4 intradermal injections of 1.0 cc each (2 injections per cell line). Each injection is completed subcutaneously by the intradermal space. On vaccination day subsequent to Day 0, the injection sites are rotated. A total dose of $1.2 \times 10^8$ cells, divided into 4 injections, is being given once every week for 8 weeks.

During the treatment cycle, evaluations for local systemic reaction to the vaccination are performed on the day of vaccination (Week 1, 2, 3, 4, 5, 6, 7 and 8). Starting from the first vaccination, PSA measurements are determined every month for 4 months, and then every 4 months for two years in Part 2 of the study. PSA levels are drawn more frequently than every 4 months if clinically indicated. A blood sample for PCR testing is drawn prior to the first vaccination. The final visit for Part 1 occurs two weeks after administration of the last vaccination (week 8).

Enrolled patients who have received at least one vaccination participate in long term follow-up evaluations with their PSA checks. They will have a yearly physical examination and clinical evaluation thereafter, or more frequently as clinically indicated until the patient dies or until allogeneic prostate cancer cell line vaccines are approved by the FDA.

2. Identification of Novel Tumor-Associated Antigens

A. Preparation of Sera

Sera used for the studies were prepared from the blood drawn from the patients in autologous or allogeneic prostate GVAX® vaccine trials two hours before vaccination and two weeks after final vaccination.

B. Preparation of Cell Lysates

Primary cell lines derived from prostate stromal, prostate epithelia, prostate smooth muscle, and lung fibroblast, were purchased from Clontenics (San Diego, Calif.) and were grown in SCGM, PrEGM, SmGM, and FGM-2 medium (Clontenics, San Diego, Calif.). Cells were grown in the DMEM+F12 medium (JHR bioscience, Lenexa, Kans.) containing 10% fetal calf serum, penicillium/strepavidin, and glutamine. When cell density reached 80% confluence in T-175 flasks (Becton, Dickinson & Company, Franklin Lakes, N.J.), cells were washed two times with PBS followed by incubation in Versene (Gibco BRL, Grand Island, N.Y.) for 10-30 minutes to detach the cells from the flasks. The cells were then harvested and spun down in table-top centrifuge (CS-6R, Beckman, Palo Alto, Calif.) at 1,000 rpm for 10 minutes. Cells were washed three times with PBS. For non-adherent cells (Jurkat and peripheral blood cells), cells were harvested, spun down, and washed three times with PBS. After washing, $2 \times 10^7$ cells were lysed with 1 ml of lysis buffer (10 mM Tris pH 7.4, 1 mM EDTA, 10% glycerol, 1% NP40, 1 mM PMSF, and 1% protease inhibitor cocktail set III (Cat. 539134, Calbiochem, San Diego, Calif.)), followed by incubation on ice for one hour. Insoluble cell debris was then removed by centrifugation using a table-top eppendorf centrifuge at 4° C. for 30 minutes. The supernatant was removed and the protein concentration measured by BCA (Pierce, Rockford, Ill.).

C. Western Blot Analysis:

Indicated amounts of protein.(25-35 µg/lane) in cell lysates or purified PSA (Calibiochem, San Diego, Calif.) or other cancer-associated markers were separated on a 4-20% gradient SDS-PAGE (Norvex, San Diego, Calif.), followed by electro-transferring to a nitrocellulose membrane (Norvex, San Diego, Calif.) in a transblot apparatus (Xcell II, Blot Module, Norvex, San Diego, Calif.) at 25 mV constant voltage for 2-3 hours. After transferring, the nitrocellulose membrane was blotted with blocking solution (10% non-fat milk in 0.05% Tween 20 in PBS) overnight at 4° C. After overnight blocking, the membrane was incubated with patients' serum (1:1000 dilution in PBS+0.05% Tween 20) at room temperature for 2 hours followed by five washes with PBS+0.1% Tween 20. HPRT-conjugated goat anti-human IgM+G+A (Zymed, South San Francisco, Calif., 1:3000 dilution in PBS+0.05% Tween 20) was incubated with membrane for one hour followed by six washes with PBS+0.1% Tween 20. The results were developed by chemifluorescence (e.g., using the ECL Western blotting system, Amersham Life Science, Arlington Heights, Ill.).

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method of identifying in a biological sample from a first subject the presence of a prostate tumor-associated antigen that does not cross-react immunologically with antibodies that cross-react immunologically with prostate-specific antigen, comprising the steps of:
   obtaining sera from a second subject, said second subject suffering from prostate cancer;
   administering to said second subject a composition comprising allogeneic prostate cancer cells that have been genetically engineered to express GM-CSF and rendered proliferation-incompetent;
   obtaining sera from said second subject following administration of said composition;
   contacting said biological sample with sera obtained prior to and following administration of said composition;
   identifying in a Western blot the presence of the prostate-tumor-associated antigen in said biological sample as a result of said antigen binding to the sera obtained following administration of said composition but not binding to the sera obtained prior to administration of said composition.

2. The method of claim 1, wherein said proliferation-incompetent cancer cells are LnCaP or PC3 cells.

3. The method of claim 1, wherein said proliferation-incompetent cancer cells are LnCaP and PC3 cells.

4. The method of claim 1, wherein said first and second subjects are human.

5. The method of claim 1, wherein said composition is administered intradermally, intramuscularly, or subcutaneously via injection.

6. The method of claim 5, wherein said composition is administered intradermally.

* * * * *